United States Patent
Butters et al.

(10) Patent No.: US 7,081,747 B2
(45) Date of Patent: Jul. 25, 2006

(54) SYSTEM AND METHOD FOR CHARACTERIZING A SAMPLE BY LOW-FREQUENCY SPECTRA

(75) Inventors: John T. Butters, Langley, WA (US); Bennett M. Butters, Lacey, WA (US); Lisa C. Butters, Langley, WA (US)

(73) Assignee: Nativis, Inc., La Jolla, CA (US)

( * ) Notice: Subject to any disclaimer, the term of this patent is extended or adjusted under 35 U.S.C. 154(b) by 146 days.

(21) Appl. No.: 10/923,545

(22) Filed: Aug. 20, 2004

(65) Prior Publication Data

US 2005/0030016 A1    Feb. 10, 2005

Related U.S. Application Data

(63) Continuation of application No. PCT/US03/09544, filed on Mar. 28, 2003.

(51) Int. Cl.
*G01R 33/02* (2006.01)
(52) U.S. Cl. ............... 324/248; 324/244; 702/75
(58) Field of Classification Search ........ 324/247–249, 324/244, 228, 239; 600/409; 326/5; 505/162, 505/845–846; 702/75–77
See application file for complete search history.

(56) References Cited

U.S. PATENT DOCUMENTS

| | | | |
|---|---|---|---|
| 4,031,462 A | 6/1977 | Bouvier et al. |
| 4,095,168 A | 6/1978 | Hlavka |
| 4,365,303 A | 12/1982 | Hannah |
| 4,682,027 A | 7/1987 | Wells |
| 4,692,685 A | 9/1987 | Blaze |
| 4,751,515 A | 6/1988 | Corum |
| 4,822,169 A | 4/1989 | Distl et al. |
| 5,254,950 A | 10/1993 | Fan et al. |
| 5,343,147 A | 8/1994 | Sager et al. |
| 5,446,681 A | 8/1995 | Gethner |
| 5,458,142 A | 10/1995 | Farmer et al. |
| 5,465,049 A | 11/1995 | Matsuura et al. |
| 5,508,203 A | 4/1996 | Fuller et al. |
| 5,541,413 A | 7/1996 | Pearson et al. |
| 5,574,369 A | 11/1996 | Hibbs |

(Continued)

FOREIGN PATENT DOCUMENTS

WO    WO 87/02981 A1    5/1987

(Continued)

OTHER PUBLICATIONS

Atkins, P.W., "Rotational and Vibrational Spectra," Physical Chemistry, 1990, pp. 458-497, Oxford University Press, Oxford, UK.

(Continued)

*Primary Examiner*—Jay M. Patidar
(74) *Attorney, Agent, or Firm*—Perkins Coie LLP

(57) ABSTRACT

A method and apparatus for interrogating a sample that exhibits molecular rotation are disclosed. In practicing the method, the sample is placed in a container having both magnetic and electromagnetic shielding, and Gaussian noise is injected into the sample. An electromagnetic time-domain signal composed of sample source radiation superimposed on the injected Guassian noise is detected, and this signal is cross-correlated with a second time-domain signal produced by the same or similar sample, to produce a cross-correlated signal with frequency domain components. The latter is plotted in the frequency domain by a fast Fourier transform to produce a frequency domain spectrum in a frequency range within DC to 50 KHz. From this spectrum, one or more low-frequency signal components that are characteristic of the sample being interrogated are identified.

27 Claims, 19 Drawing Sheets

U.S. PATENT DOCUMENTS

| | | | |
|---|---|---|---|
| 5,583,432 | A | 12/1996 | Barnes |
| 5,656,937 | A | 8/1997 | Cantor |
| 5,696,691 | A | 12/1997 | Schlosser et al. |
| 5,734,353 | A | 3/1998 | Van Voorhies |
| 5,752,514 | A | 5/1998 | Okamura et al. |
| 5,789,961 | A | 8/1998 | Bulsara et al. |
| 5,944,782 | A | 8/1999 | Noble et al. |
| 5,952,978 | A | 9/1999 | VanVoorhies |
| 5,955,400 | A | 9/1999 | Yokosawa et al. |
| 5,959,548 | A | 9/1999 | Smith |
| 6,020,782 | A | 2/2000 | Albert et al. |
| 6,028,558 | A | 2/2000 | Van Voorhies |
| 6,084,399 | A | 7/2000 | Nagaishi et al. |
| 6,136,541 | A | 10/2000 | Gulati |
| 6,142,681 | A | 11/2000 | Gulati |
| 6,150,812 | A | 11/2000 | Pinsky et al. |
| 6,159,444 | A | 12/2000 | Schlenga et al. |
| 6,196,057 | B1 | 3/2001 | Discenzo |
| 6,204,821 | B1 | 3/2001 | Zhu et al. |
| 6,285,249 | B1 | 9/2001 | Bulsara et al. |
| 6,320,369 | B1 | 11/2001 | Hidaka et al. |
| 6,323,632 | B1 | 11/2001 | Husher et al. |
| 6,541,978 | B1 | 4/2003 | Benveniste et al. |
| 6,724,188 | B1 | 4/2004 | Butters |
| 6,760,674 | B1 | 7/2004 | Bombard |
| 6,885,192 | B1 | 4/2005 | Clarke et al. |
| 6,952,652 | B1* | 10/2005 | Butters ................. 702/27 |
| 6,995,558 | B1* | 2/2006 | Butters et al. ............ 324/244 |
| 2003/0016010 | A1 | 1/2003 | Kandori |
| 2004/0174154 | A1 | 9/2004 | Butters |
| 2004/0183530 | A1 | 9/2004 | Butters |
| 2004/0222789 | A1 | 11/2004 | Pinsky et al. |
| 2005/0176391 | A1* | 8/2005 | Butters ................. 455/180.3 |

FOREIGN PATENT DOCUMENTS

| | | |
|---|---|---|
| WO | WO 91/13611 A1 | 9/1991 |
| WO | WO 91/14181 A1 | 9/1991 |
| WO | WO 94/17406 A1 | 8/1994 |
| WO | WO 99/54731 A1 | 10/1999 |
| WO | WO 00/01412 A1 | 1/2000 |
| WO | WO 00/17637 A1 | 3/2000 |
| WO | WO 00/17638 A1 | 3/2000 |
| WO | WO-03-83439 A2 | 10/2003 |
| WO | WO-03-102566 A2 | 12/2003 |
| WO | WO-05-036131 A2 | 4/2005 |

OTHER PUBLICATIONS

Cooley, J. et al., "An Algorithm for the Machine Calculation of Complex Fourier Series", Mathematics of Computation, Apr. 1965, pp. 297-301, vol. 19, No. 90, American Mathematical Society, Providence, Rhode Island.

Ingram, D.J.E., "Spectroscopy at Radio and Microwave Frequencies," 1967, pp. 1-16, Butterworths, London, UK.

International Search Report for International Application No. PCT/US03/11834; Apr. 2003; Applicant: WavBank, Inc.

Aissa et al., "Transatlantic Transfer of Digitized Antigen Signal by Telephone Link", Digi Bio-FASEB 97, Abstract only, <http://digibio.com/cgi-bin/node.pl?lg=us&nd=n4_3>.

Aissa, et al., Molecular signaling at high dilution or by means of electronic circuitry:, Journal of Immunology, 146A, 1994, Abstract only.

Benveniste, et al., "Digital biology: Specificity of the digitized molecular signal", FASEB Journal, A412, 1997, Abstract only, <http://digibio.com/cgi-bin/node.pl?lg=us&nd=n4_2>.

Benveniste, et al., "Digital Recording/Transmission of the Cholinergic Signal", DigiBio—FASEB 96, Abstract only, >http://digibio.com/cgi-bin/node.pl?ig=us&nd=n4_4>.

Benveniste et al., "Specific Remote Detection of Bacteria Using an Electromagnetic/Digital Procedure", FASEB Journal, vol. 13, p. A852, 1999, Abstract only, <http://digibio.com/cgi-bin/node.pl?lg=us&nd=n4_12>.

Benveniste et al., "The Molecular Signal is not Functional in the Absence of "Informed" Water", FASEB Journal, vol. 13, p. A163, 1999, Abstract only, <http://digibio.com/cgi-bin/node.pl?lg=us&nd=n4_11>.

Benveniste et al., "A Simple and Fast Method for in Vivo Demonstration of Electromagnetic Molecular Signaling (EMS) via High Dilution or Computer Recording", FASEB Journal, vol. 13, p. A163, 1999, Abstract only.

Benveniste et al., "Digital Biology: Specificity of the Digitized Molecular Signal", FASEB Journal, vol. 12, p. A412, 1998, Abstract only.

Benveniste, et al., "Electronic transmission of the cholinergic signal", FASEB Journal, A683, 1995, Abstract only.

Benveniste, et al., "Transfer of molecular signals via electronic circuitry", FASEB Journal, A602, 1993, Abstract only.

Benveniste, J., et al., "Transfer of the molecular signal by electronic amplification", FASEB Journal, A398, 1994, Abstract only.

Benveniste, J., "Molecular Signaling, What Is So Unacceptable for Ultra-Orthodox Scientists?", 2 pages, <http://www.digibio.com.cgi-bin/node.pl?nd=n5>.

Benveniste, J., "From 'Water Memory' effects To 'Digital BIology'. . . - Understanding Digital Biology", 4 pages, <http://www.digibio.com/cgi-bin/node.pl?nd=n3>, Jun. 14, 1998.

Binhi, V., "An Analytical Survey of Theoretical Studies in the Area of Magnetoreception", 11 pages, <http://www.biomag.info/survey.htm>, 1999.

Brault, J., et al., "The Analysis and Restoration of Astronomical Data via the Fast Fourier Transform", Astronomy and Astrophysics, vol. 13, No. 2, Jul. 1971, pp. 169-189.

Brigham, E., "The Fast Fourier Transform and Applications", Prentice Hall, 1988, pp. 131-145.

DigiBio S.A., Experimental models, From "Water Memory" effects to "Digital Biology", <http://digibio.com/cgi-bin/node.pl?nd=n7>.

"Direct Nanoscale Conversion of Bio-Molecular Signals Into Electronic Information" DARPA Defense Sciences Office, 2 pages, <<http://www.darpa.mil/dso/thrust/biosci/moldice.>>.

"Engineered Bio-Molecular Nano-Devices/Systems (MOLDICE)" DARPA Defense Sciences Office, 1 page, <<http://www.darpa.mil/dso/thrust/biosci/moldice.htm>>.

Chapeau-Blondeau, F., "Input-output gains for signal in noise in stochastic resonance", Physics Letters A, vol. 232, pp. 41-48, Jul. 21, 1997, Elsevier Science B.V.

Chapeau-Blondeau, F., "Periodic and Aperiodic Stochastic Resonance with Output Signal-to-Noise Ratio Exceeding That At The Input", International Journal of Bifurcation and Chaos, vol. 9, No. 1, pp. 267-272, 1999, World Scientific Publishing Company.

Duhamel, P., et al., "'Split radix' FFT algorithm", Electronics Letters, The Institution of Electrical Engineers, vol. 20, No. 1, Jan. 5, 1984, pp. 14-16.

Glanz, J., "Sharpening the Senses with Neural 'Noise'", Science, vol. 277, No. 5333, Sep. 19, 1997, 2 pages, <http://complex.gmu.edu/neural/papers/others/science97_noise.html.

Gorgun, S., "Studies on the Interaction Between Electromagnetic Fields and Living Matter Neoplastic Cellular Culture.", 22 pages, <http://bodyvibes.com/study1.htm>.

Hoffman, F., "An Introduction to Fourier Theory", 10 pages, <http://aurora.phys.utk.edu/~forrest/papers/fourier/index.html>.

Kaufman, I. et al., "Zero-dispersion stochastic resonance in a model for a superconducting quantum interference device", Physical Review E, vol. 57, No. 1, pp. 78-87, Jan. 1998, The American Physical Society.

Nokazi, D., et al., "Effects of Colored Noise on Stochastic Resonance in Sensory Neurons", Physical Review Letters, The American Physical Society, vol. 82, No. 11, Mar. 15, 1999, 4 pages.

Oppenheim, et al., "Digital Signal Processing", Prentice-Hall, 1975, ISBN 0-13-214635-5, pp. 87-121.

Proakis, J.G., et al., "Advanced digital signal processing", Maxwell MacMillan, 1992, pp. 31-57.

Soma, R., "Noise Outperforms White Noise in Sensitizing Baroreflex Function in the Human Brain", Physical Review Letters, vol. 91, No. 7, 4 pages, Aug. 15, 2003, The American Physical Society.

"The First International Workshop on TFF; What is Biophysies Behind?", Abstract Booklet, Jun. 15, 1996, 18 pages, <http://www.biophysics.nl/idras.htm>.

Thomas, Y., et al., "Activation of human neurophils by electronically transmitted phorbolmyristate acetate", Medical Hypotheses, vol. 54, No. 1, pp. 33-39.

Thomas, et al., "Direct transmission to cells of a molecular signal via an electronic device", FASEB Journal, A227, 1995, Abstract only.

Thomas, et al., "Modulation of Human Neutrophil Activation by "Electronic" Phorbol Myristate Acetate (PMA)", DigiBio, Abstract only, <http://www.digibio.com/cgi-bin/node.pl?lg=us&nd=n4_5>.

Turin, L., "A spectroscopic mechanism for primary olfactory reception", Chemical Senses, vol. 21, No. 6, pp. 773-791.

Weaver, J., et al., "The response of living cells to very weak electrip fields: the thermal noise limit.", National Library of Medicine, 2 pages, Mar. 2, 1990, <http://www.ncbi.nlm.nih.gov/entrez/query.fcgi?db=PubMed&cmd=Retrieve&list_uids=2300806&dopt=Citation=.

* cited by examiner

SYSTEM AND METHOD FOR CHARACTERIZING A SAMPLE BY LOW-FREQUENCY SPECTRA

CROSS-REFERENCE TO RELATED APPLICATIONS

This application is a continuation of International Application No. PCT/US03/09544 filed Mar. 28, 2003 and claims priority to U.S. application Ser. No. 10/112,927 filed Mar. 29, 2002 (now U.S. Pat. No. 6,724,188 Issued Apr. 20, 2004), both of which are incorporated herein in their entireties by reference.

BACKGROUND

There are a variety of spectroscopic tools for characterizing atomic or molecular compound. These include, but are not limited to, x-ray, UV, visible-light, infrared and microwave spectroscopy, and nuclear and electron spin resonance (NMR and ESR) spectroscopy. In general, spectroscopic tools are useful for at least four different type of chemical-analytical problems: first, to characterize an atomic and molecular compound according to its spectrographic features, e.g., spectral components; second, to determine the atomic composition of a compound, according to the spectral characteristics of atoms making up the compound; third, to determine 2-D or 3-D conformation of a molecular compound according to the spectral characteristic of atom-atom interactions in the compound; and fourth, to detect and identify components, e.g., contaminants, in a sample according to the distinguishing spectral characteristics of the compound being detected.

Most existing spectroscopic tools provide some unique advantage(s) in terms of sensitivity, the information gained, ease of measurement and cost. Because each tool provides information not otherwise available, it is generally advantageous to be able to bring to bear on any chemical-analytical, as many pertinent spectroscopic tools as possible.

SUMMARY

The invention includes, in one aspect, an apparatus for interrogating a sample that exhibits molecular rotation. The apparatus includes a sample container having both magnetic and electromagnetic shielding, a source of Gaussian noise for injection into the sample, a detector for detecting an electromagnetic time-domain signal composed of sample source radiation superimposed on the injected Gaussian noise, and a storage device for storing the time-domain signal and a time-domain signal separately detected from the same or a similar sample.

An electronic computer performs the following signal processing operations on the stored signals from the storage device, and performs the following signal processing and output operations: (i) cross correlating the time-domain signal detected with second time-domain signal, to produce a frequency domain spectrum in a frequency range within DC to 50 Khz, and (ii) generating an output that includes information relating to low-frequency spectral components in the spectrum that are characteristic of the sample.

The container may be an attenuation tube having a sample-holding region, a magnetic shielding cage surrounding the sample region, and a Faraday cage contained within the magnetic shielding cage and also surrounding the sample region. The sample container may include a temperature controller for maintaining the sample in the container at a selected temperature.

The source of Gaussian noise may include a Gaussian noise generator and a Helmholz coil which is contained within the magnetic cage and the Faraday cage, and which receives a noise output signal from the noise generator. The injector is preferably designed to inject stationary white Gaussian noise into the sample, at an amplitude sufficient to produce non-stationary composite signal components. A preferred injected white-noise frequency is between DC and 2 KHz.

The detector in the apparatus may include a first-derivative superconducting gradiometer that outputs a current signal, and a SQUID operatively connected to the gradiometer to convert the current signal to an amplified voltage signal. The detector may further include, for use in removing stationary noise components in the time-dependent signal, a signal inverter operatively connected to the noise source and to the SQUID, for receiving Gaussian noise from the noise source and outputting into the SQUID, Gaussian noise in inverted form with respect to the Gaussian noise injected into the sample.

The cross-correlated frequency spectrum may be Fourier transformed to produce a plot of sample components as a function of frequency, where the correlation values are represented as spectral-component amplitudes. The frequency domain generated preferably within the range between DC to 6.5 Kz. One exemplary range for observing low-frequency signal components is 100 and 1,200 Hz.

The computer may be operable, in generating an output, of identifying the frequencies of low-frequency signal components in a spectrum whose cross-correlated spectral correlations have a selected statistical measure above background spectral noise. This feature is useful for example, in characterizing a known sample material in terms of its low-frequency signal components.

For use in identifying one or more components in a sample, the electronic computer may be operable, in generating an output, to (a) identify the frequencies of sample signal components (i) in a selected frequency range between DC and 50 KHz (ii) whose cross-correlated spectral correlations have a selected statistical measure above background spectral noise, (b) compare such sample signal-components with characteristic low-frequency signal components of known compounds suspected of being present in the sample, and (c) identify a compound as being present in the sample if its characteristic low-frequency signal frequencies correspond to those one or more of the sample-signal frequencies.

The apparatus is used in practicing a method for interrogating a sample that exhibits molecular rotation, in accordance with another aspect of the invention. Where the method is used in identifying one or more components in a liquid sample, detection of the component(s) may be at the part per million and part per 10 billion level.

In some cases, one or more of the low-frequency signal components of a compound may exhibit a concentration-dependent frequency shift, typically in the range of less than 2 Hz. In this embodiment, identifying a compound may include approximating the concentration of a sample component by its frequency shift. In some cases, one or more of the low-frequency signal components of a compound may exhibit a concentration-dependent cross-spectral correlation. In this embodiment, identifying a compound may include approximating the concentration of the compound from its cross-spectral correlation.

Also disclosed is a low-frequency spectral signature associated with a material of interest. The signature includes a list or tabulation of frequency components in the dc-50 khz frequency range that are generated by the method above, and preferably includes those components whose amplitudes have a selected statistical measure above background spectral noise.

In still another aspect, the invention includes a time-domain signal associated with a material of interest, produced by the steps of:

placing the sample of the material in a container having both magnetic and electromagnetic shielding, injecting Gaussian noise into the sample; and recording an electromagnetic time-domain signal composed of sample source radiation superimposed on the injected Gaussian noise.

The signal may be used, for example, in generating a low frequency signal signature associated with a material of interest, in accordance with the method above.

These and other objects and features of the invention will become more fully apparent when the following detailed description of the invention is read in conjunction with the accompanying drawings

Figure 1:
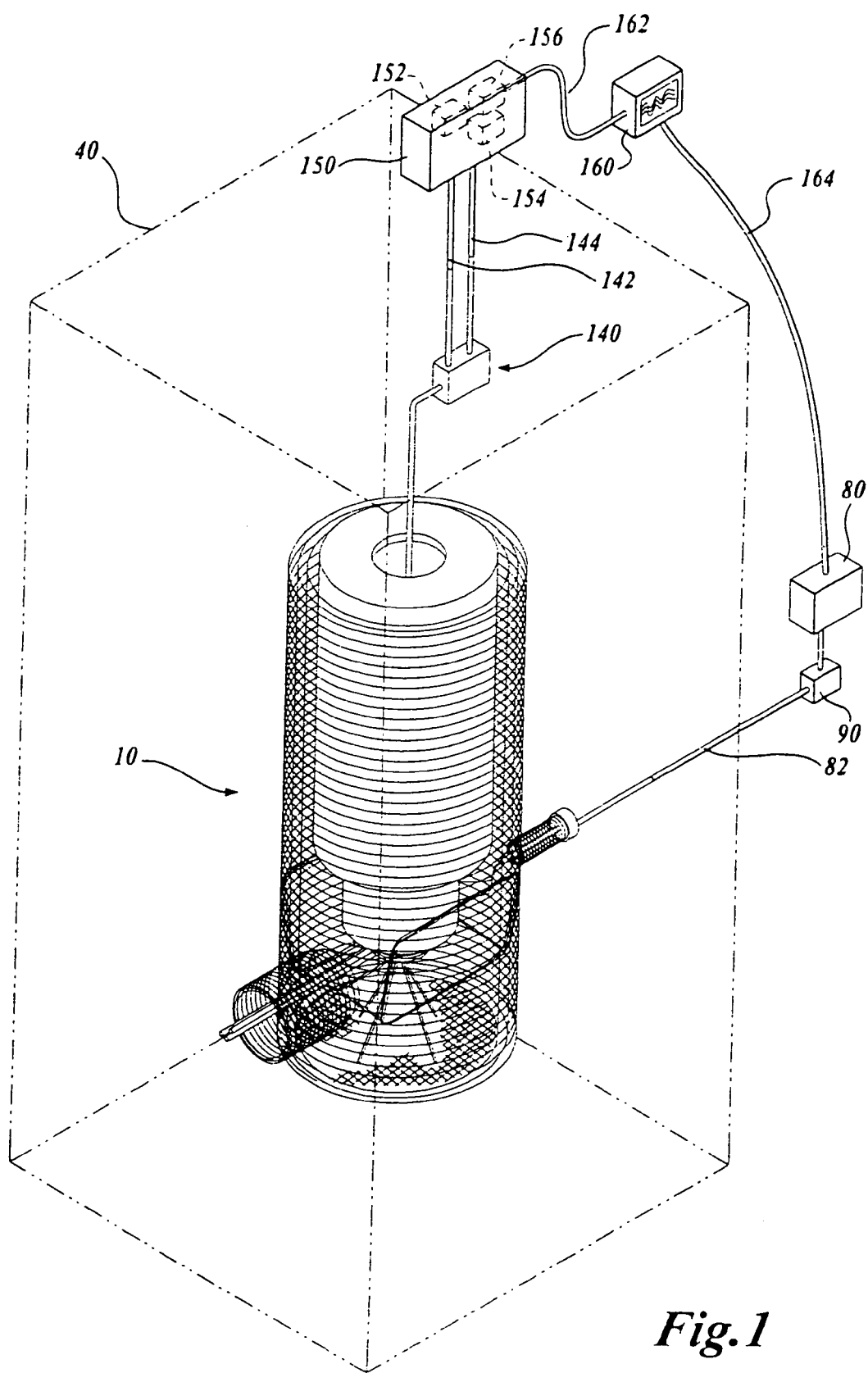
FIG. 1 is an isometric view of one embodiment of a molecular electromagnetic signaling detection apparatus formed in accordance with one embodiment of the present invention.

In the drawings, identical reference numbers identify identical or substantially similar elements or acts. To easily identify the discussion of any particular element or art, the most significant digit or digits in a reference number refer to the figure number in which that element is first introduced.

DETAILED DESCRIPTION

I. Definitions

The terms below have the following definitions unless indicated otherwise.

"Sample that exhibits molecular rotation" refers to a sample material, which may be in gaseous, liquid or solid form (other than a solid metal) in which one or more of the molecular compounds or atomic ions making up or present in the sample exhibit rotation.

"Magnetic shielding" refers to shielding that inhibits or prevents passage of magnetic flux as a result of the magnetic permeability of the shielding material.

"Electromagnetic shielding" refers to, e.g., standard Faraday electromagnetic shielding.

"Time-domain signal" or 'time-series signal" refers to a signal with transient signal properties that change over time.

"Sample-source radiation" refers to magnetic flux emissions resulting from the molecular motion of a sample, such as the rotation of a molecular dipole in a magnetic field.

"Gaussian noise" means random noise having a Gaussian power distribution.

"Stationary white Gaussian noise" means random Gaussian noise that has no predictable future components.

"Frequency-domain spectrum" refers to a Fourier frequency plot of a time-domain signal.

"Spectral components" refer to singular or repeating qualities within a time-domain signal that can be measured in the frequency, amplitude, and/or phase domains. Spectral components will typically refer to signals present in the frequency domain.

"Similar sample," with reference to a first sample, refers to the same sample or a sample having substantially the same sample components as the first sample.

"Faraday cage" refers to an electromagnetic shielding configuration that provides an electrical path to ground for unwanted electromagnetic radiation, thereby quieting an electromagnetic environment.

II. Apparatus

Described in detail below is a system and method for detecting, processing, and presenting low frequency electromagnetic emissions or signals of a sample of interest. In one embodiment, a known white or Gaussian noise signal is introduced to the sample. The Gaussian noise is configured to permit the electromagnetic emissions from the sample to be sufficiently detected by a signal detection system. Sets of detected signals are processed together to ensure repeatability and statistical relevance. The resulting emission pattern or spectrum can be displayed, stored, and/or identified as a particular substance.

The following description provides specific details for a thorough understanding of, and enabling description for, embodiments of the invention. However, one skilled in the art will understand that the invention may be practiced without these details. In other instances, well-known structures and functions have not been shown or described in detail to avoid unnecessarily obscuring the description of embodiments of the invention.

As explained in detail below, embodiments of the present invention are directed to providing an apparatus and method for the repeatable detection and recording of low-threshold molecular electromagnetic signals. A magnetically shielded faraday cage shields the sample material and detection apparatus from extraneous electromagnetic signals. Within the magnetically shielded faraday cage, a coil injects white or Gaussian noise, a nonferrous tray holds the sample, and a gradiometer detects low-threshold molecular electromagnetic signals. The apparatus further includes a superconducting quantum interference device ("SQUID") and a preamplifier.

The apparatus is used by placing a sample within the magnetically shielded faraday cage in close proximity to the noise coil and gradiometer. White noise is injected through the noise coil and modulated until the molecular electromagnetic signal is enhanced through stochastic resonance. The enhanced molecular electromagnetic signal, shielded from external interference by the faraday cage and the field generated by the noise coil, is then detected and measured by the gradiometer and SQUID. The signal is then amplified and transmitted to any appropriate recording or measuring equipment.

Referring to FIG. 1, there is shown a shielding structure 10 which includes, in an outer to inner direction, a conductive wire cage 16 which is a magnetic shield and inner conductive wire cages 18 and 20 which provide electromagnetic shielding. In another embodiment, the outer magnetic shield is formed of a solid aluminum plate material having an aluminum-nickel alloy coating, and the electromagnetic shielding is provided by two inner wall structures, each formed of solid aluminum.

Figure 2:
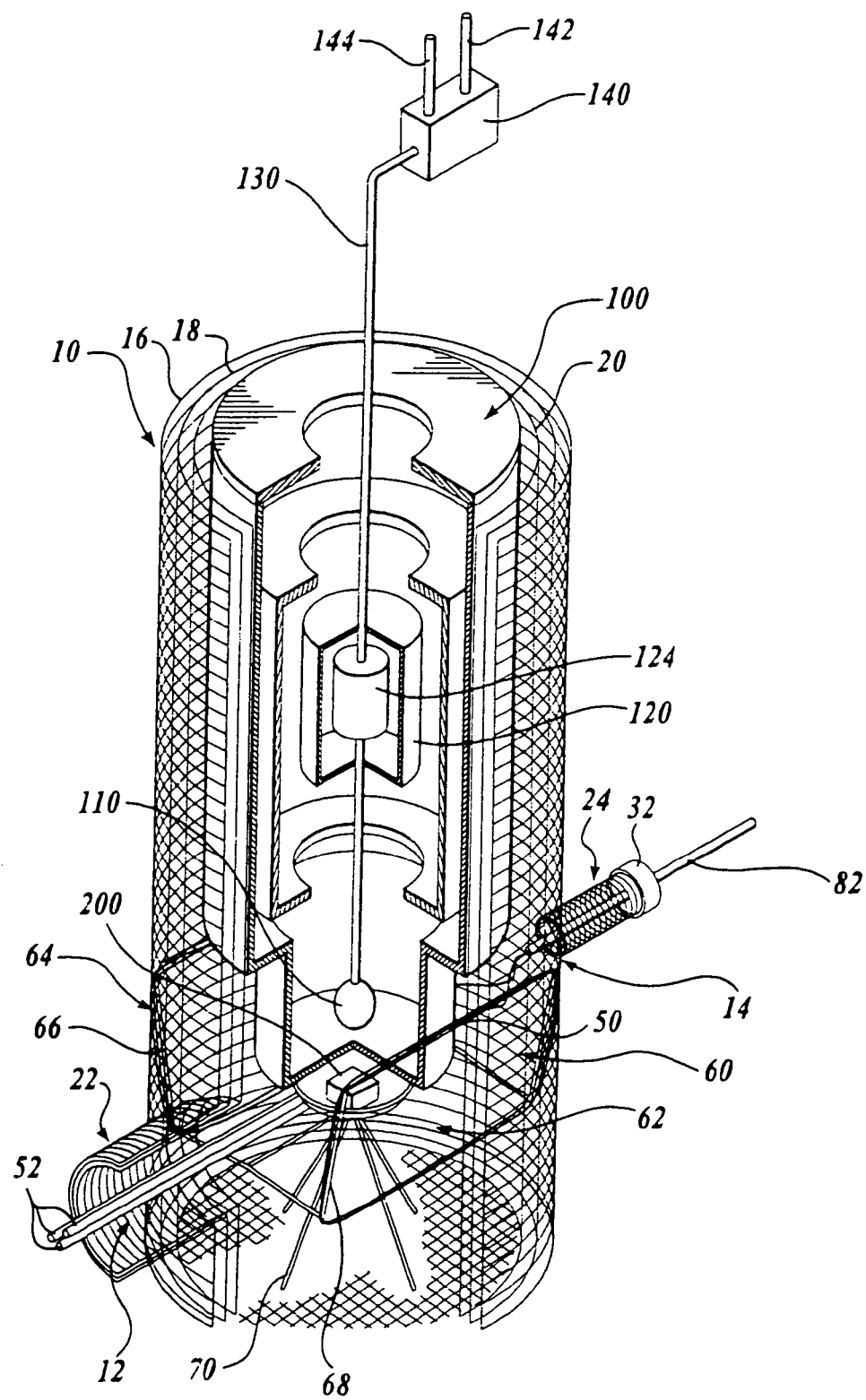
FIG. 2 is an enlarged, detail view of the faraday cage and its contents shown in FIG. 1.

Referring to FIG. 2, the faraday cage 10 is open at the top, and includes side openings 12 and 14. The faraday cage 10 is further comprised of three copper mesh cages 16, 18 and 20, nestled in one another. Each of the copper mesh cages 16, 18 and 20 is electrically isolated from the other cages by dielectric barriers (not shown) between each cage.

Figure 3:
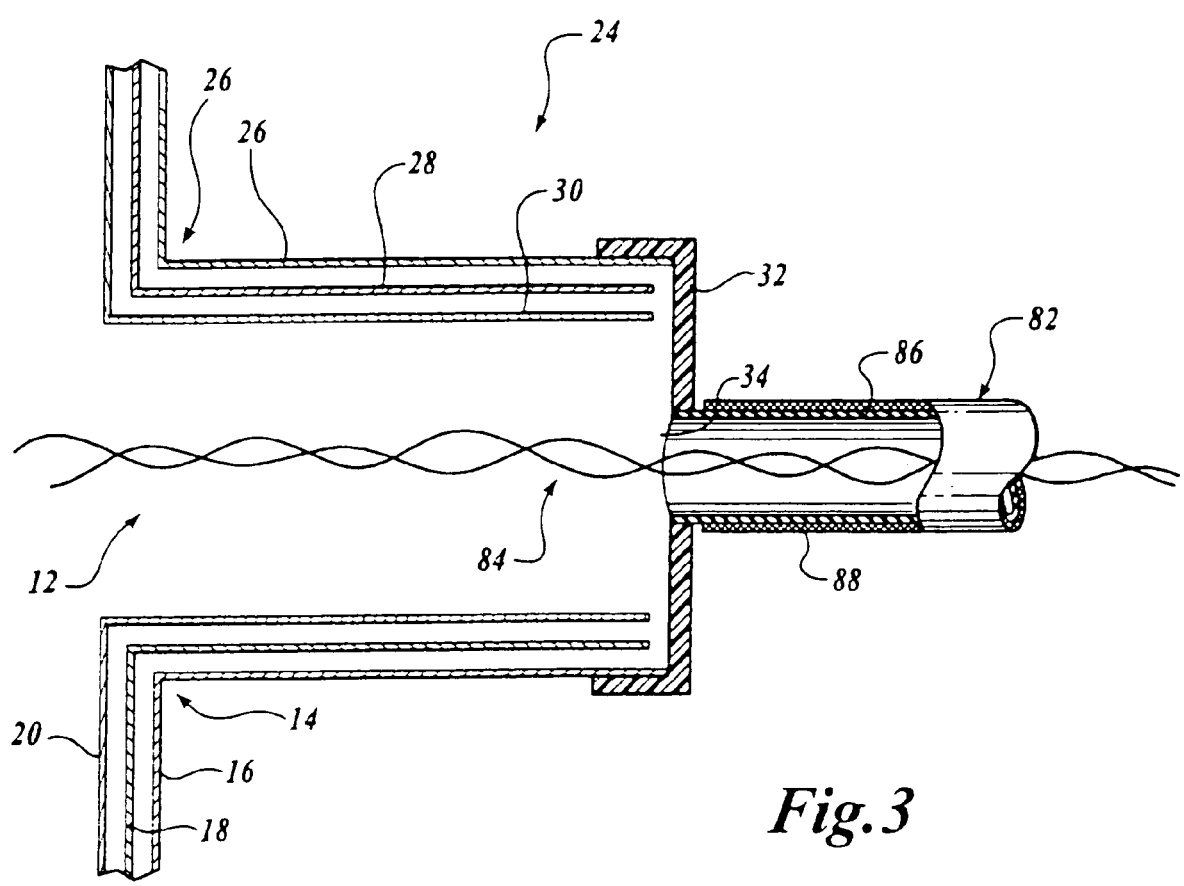
FIG. 3 is an enlarged, cross sectional view of one of the attenuation tubes shown in FIGS. 1 and 2.

Side openings 12 and 14 further comprise attenuation tubes 22 and 24 to provide access to the interior of the faraday cage 10 while isolating the interior of the cage from external sources of interference. Referring to FIG. 3, attenuation tube 24 is comprised of three copper mesh tubes 26, 28 and 30, nestled in one another. The exterior copper mesh cages 16, 18 and 20 are each electrically connected to one of the copper mesh tubes 26, 28 and 30, respectively. Attenuation tube 24 is further capped with cap 32, with the cap having hole 34. Attenuation tube 22 is similarly comprised of copper mesh tubes 26, 28 and 30, but does not include cap 32.

Referring again to FIG. 2, a low-density nonferrous sample tray 50 is mounted in the interior of the faraday cage 10. The sample tray 50 is mounted so that it may be removed from the faraday cage 10 through the attenuation tube 22 and side opening 12. Three rods 52, each of which is greater in length than the distance from the center vertical axis of the faraday cage 10 to the outermost edge of the attenuation tube 22, are attached to the sample tray 50. The three rods 52 are adapted to conform to the interior curve of the attenuation tube 22, so that the sample tray 50 may be positioned in the center of the faraday cage 10 by resting the rods in the attenuation tube. In the illustrated embodiment, the sample tray 50 and rods 52 are made of glass fiber epoxy. It will be readily apparent to those skilled in the art that the sample tray 50 and rods 52 may be made of other nonferrous materials, and the tray may be mounted in the faraday cage 10 by other means, such as by a single rod.

Referring again to FIG. 2, mounted within the faraday cage 10 and above the sample tray 50 is a cryogenic dewar 100. In the disclosed embodiment, the dewar 100 is adapted to fit within the opening at the top of faraday cage 10 and is a Model BMD-6 Liquid Helium Dewar manufactured by Tristan Technologies, Inc. The dewar 100 is constructed of a glass-fiber epoxy composite. A gradiometer 110 with a very narrow field of view is mounted within the dewar 100 in position so that its field of view encompasses the sample tray 50. In the illustrated embodiment, the gradiometer 110 is a first order axial detection coil, nominally 1 centimeter in diameter, with a 2% balance, and is formed from a superconductor. The gradiometer can be any form of gradiometer excluding a planar gradiometer. The gradiometer 110 is connected to the input coil of one low temperature direct current superconducting quantum interference device ("SQUID") 120. In the disclosed embodiment, the SQUID is a Model LSQ/20 LTS dc SQUID manufactured by Tristan Technologies, Inc. It will be recognized by those skilled in the art that high temperature or alternating current SQUIDs can be used without departing from the spirit and scope of the invention. In an alternative embodiment, the SQUID 120 includes a noise suppression coil 124.

The disclosed combination of gradiometer 110 and SQUID 120 have a sensitivity of 5 microTesla/$\sqrt{Hz}$ when measuring magnetic fields.

The output of SQUID 120 is connected to a Model SP Cryogenic Cable 130 manufactured by Tristan Technologies, Inc. The Cryogenic Cable 130 is capable of withstanding the temperatures within and without the dewar 100 and transfers the signal from the SQUID 120 to Flux-Locked Loop 140, which is mounted externally to the faraday cage 10 and dewar 100. The Flux-Locked Loop 140 in the disclosed embodiment is an iFL-301-L Flux Locked Loop manufactured by Tristan Technologies, Inc.

Referring to FIG. 1, the Flux Locked Loop 140 further amplifies and outputs the signal received from the SQUID 120 via high-level output circuit 142 to an iMC-303 iMAG® SQUID controller 150. The Flux-Locked Loop 140 is also connected via a model CC-60 six meter fiber-optic composite connecting cable 144 to the SQUID controller 150. The fiber-optic connecting cable 144 and SQUID controller 150 are manufactured by Tristan Technologies, Inc. The controller 150 is mounted externally to the magnetic shielding cage 40. The fiber-optic connecting cable 144 carriers control signals from the SQUID controller 150 to the Flux Locked Loop 140, further reducing the possibility of electromagnetic interference with the signal to be measured. It will be apparent to those skilled in the art that other Flux-Locked Loops, connecting cables, and Squid controllers can be used without departing from the spirit and scope of the invention.

The SQUID controller 150 further comprises high resolution analog to digital converters 152, a standard GP-IB bus 154 to output digitalized signals, and BNC connectors 156 to output analog signals. In the illustrated embodiment, the BNC connectors are connected to a dual trace oscilloscope 160 through patch cord 162.

Referring to FIG. 2, a two-element Helmholtz transformer 60 is installed to either side of the sample tray 50 when the sample tray is fully inserted within the faraday cage 10. In the illustrated embodiment, the coil windings 62 and 64 of the Helmholtz transformer 60 are designed to operate in the direct current to 50 kilohertz range, with a center frequency of 25 kilohertz and self-resonant frequency of 8.8 megahertz. In the illustrated embodiment, the coil windings 62 and 64 are generally rectangular in shape and are approximately 8 inches tall by 4 inches wide. Other Helmholtz coil shapes may be used but should be shaped and sized so that the gradiometer 110 and sample tray 50 are positioned within the field produced by the Helmholtz coil. Each of coil windings 62 and 64 is mounted on one of two low density nonferrous frames 66 and 68. The frames 66 and 68 are hingedly connected to one another and are supported by legs 70. Frames 66 and 68 are slidably attached to legs 70 to permit vertical movement of the frames in relation to the lower portion of dewar 100. Movement of the frames permits adjustment of the coil windings 62 and 64 of the Helmholtz transformer 60 to vary the amplitude of white noise received at gradiometer 110. The legs 70 rest on or are epoxied onto the bottom of the faraday cage 10. In the illustrated embodiment, the frames 66 and 68 and legs 70 are made of glass fiber epoxy. Other arrangements of transformers or coils may be used around the sample tray 50 without departing from the spirit and scope of the invention.

Figure 4:
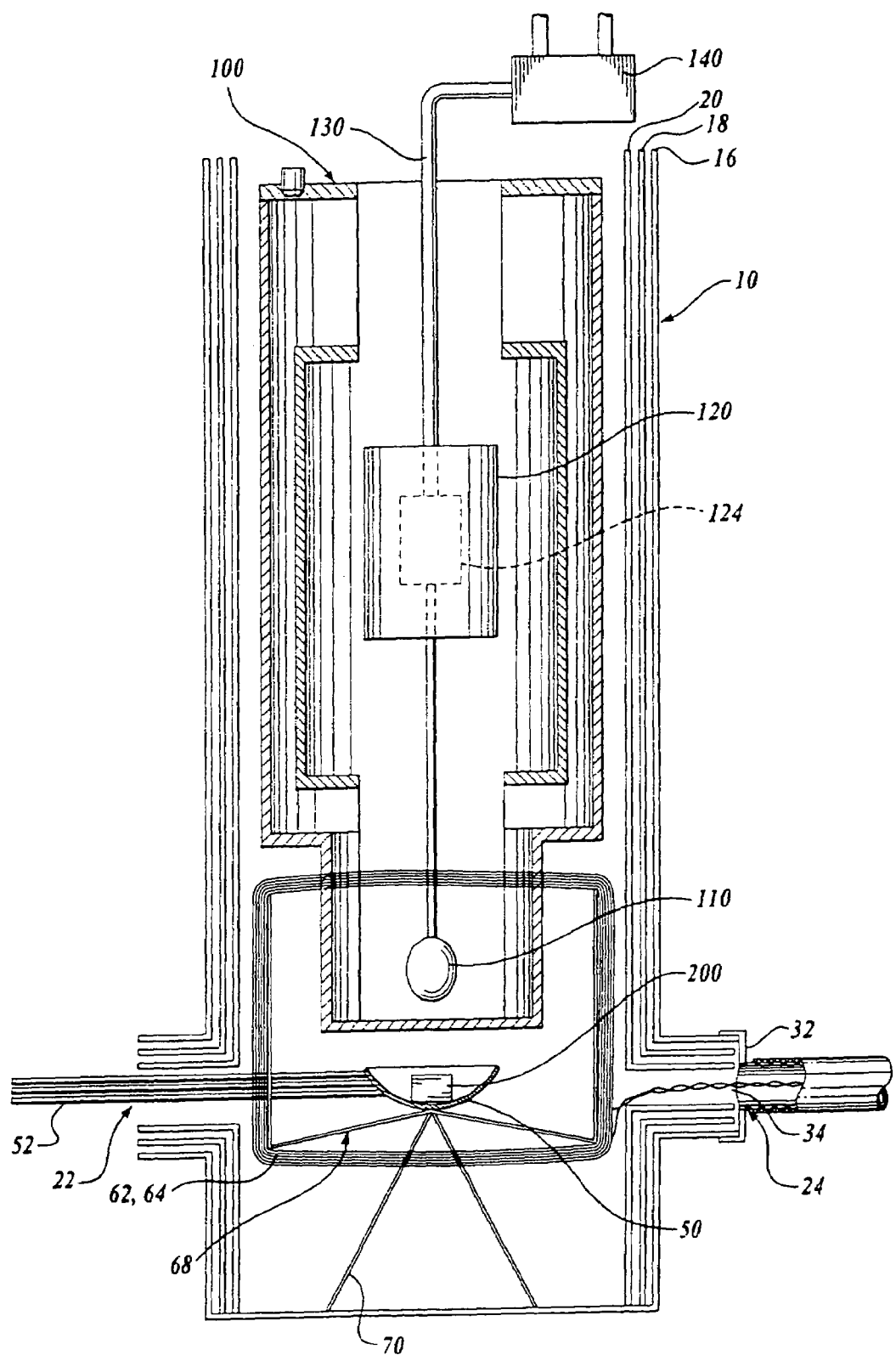
FIG. 4 is a cross-section view of the faraday cage and its contents shown in FIG. 2.

Referring to FIG. 4, there is shown a cross-sectional view of the faraday cage and its contents, showing windings 62 of Helmholtz transformer 60 in relation to dewar 100 and faraday cage 10. Note also in FIG. 4 the positioning of sample tray 50 and sample 200.

Figure 5:
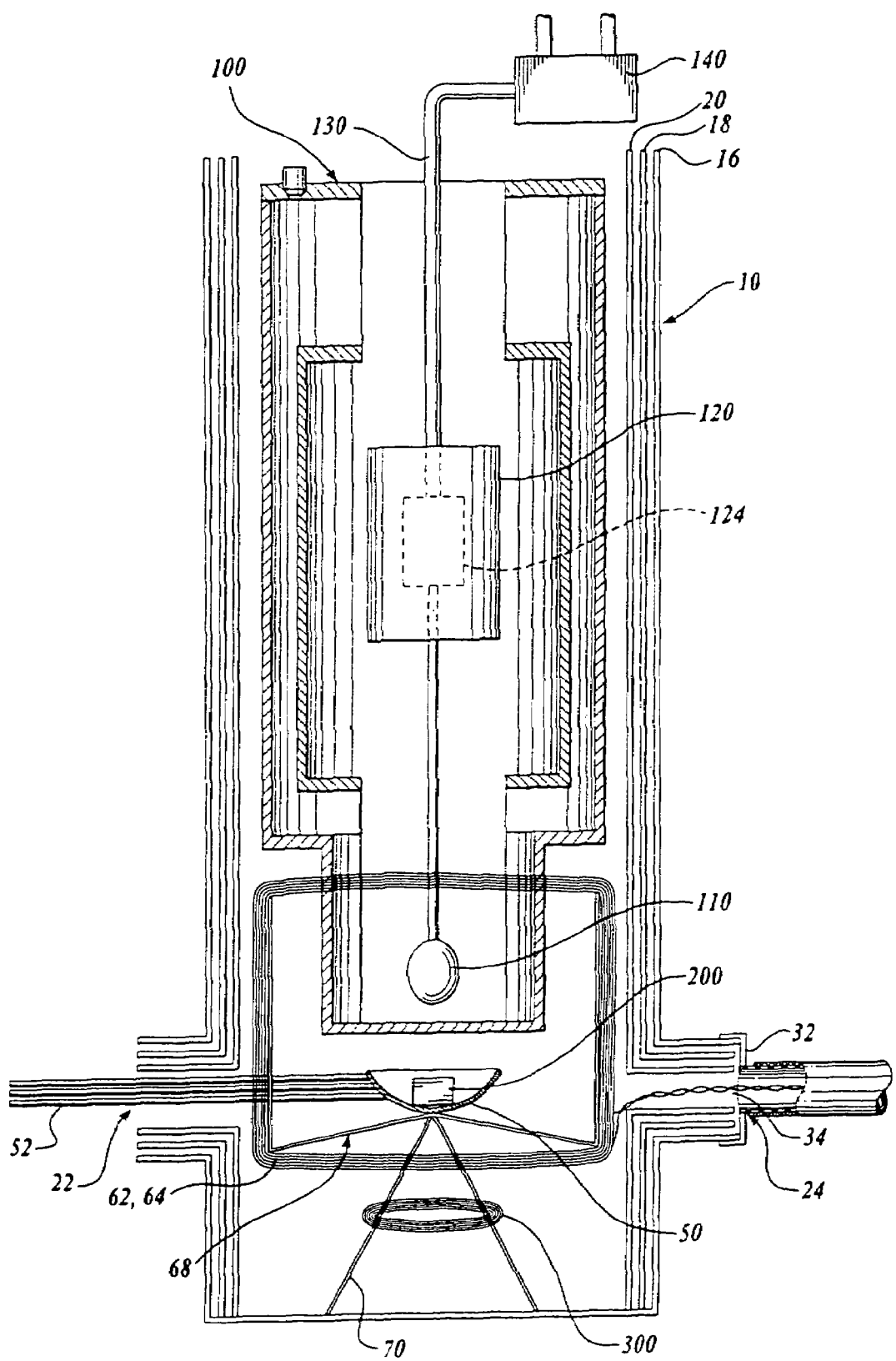
FIG. 5 is a cross-section view of an alternative embodiment of the invention shown in FIGS. 1 through 4.

Referring to FIG. 5, there is shown an alternative embodiment in which the Helmholtz coil windings 62 and 64 are fixed in a vertical orientation and an additional noise coil 300 is positioned below sample tray 50. The windings of the additional noise coil 300 are substantially perpendicular to the vertical windings 62 and 64 of Helmholtz transformer 60, and the windings of the additional noise coil 300 are thus substantially in parallel orientation to the bottom of faraday cage 10.

In this alternative embodiment, noise would be fed to noise coil 300 from an identical twisted pair wire (not shown) as that supplying the Helmholtz coil. The noise source would originate with the same noise generator used to supply noise to the Helmholtz coil. Noise would be sampled either at the noise generator via an additional noise output connection, or via a balanced splitter from an output connection to the noise generator. Attenuation of the noise signal at additional noise coil 300 would be through an adjustable RF signal attenuation circuit, of which many are available commercially, or via a suitable series of fixed value RF attenuation filters.

Figure 6:
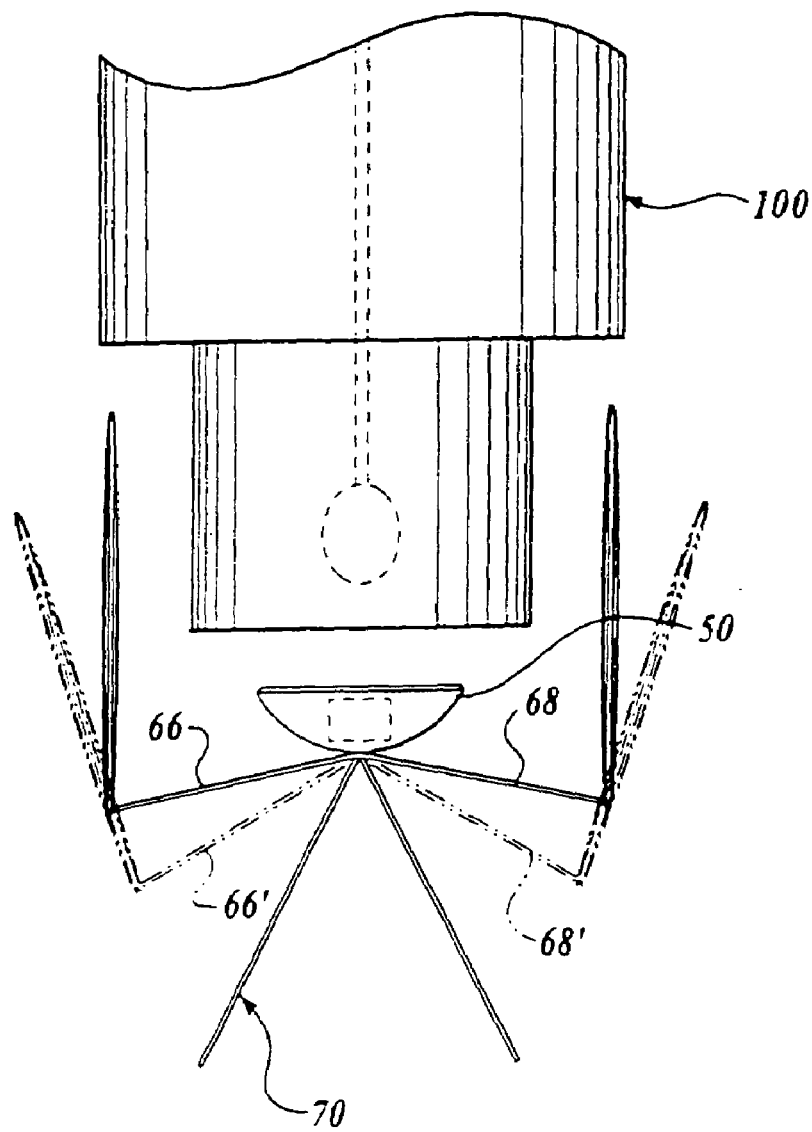
FIG. 6 is an enlarged, detail view of the frames supporting the coils of the Helmholtz transformer described herein.

Referring to FIG. 6, a detail of the frames supporting the coils of Helmholtz transformer 60 may be seen; the reference point of FIG. 6 is 90 degrees from the view of FIG. 4, and omits the faraday cage 10. Frames 66 and 68 are disposed to show the coil windings of the Helmholtz coil in a substantially vertical position and parallel to one another. Frames 66' and 68' illustrate the rotation of said frames about the axis of the hinged connection joining said frames, so as to dispose the coil windings of the Helmholtz transformer in an non-parallel relationship with one another.

Referring again to FIG. 1, an amplitude adjustable white noise generator 80 is external to magnetic shielding cage 40, and is electrically connected to the Helmholtz transformer 60 through filter 90 by electrical cable 82. Referring to FIG. 3, cable 82 is run through side opening 12, attenuation tube 24, and through cap 32 via hole 34. Cable 82 is a co-axial cable further comprising a twisted pair of copper conductors 84 surrounded by interior and exterior magnetic shielding 86 and 88, respectively. In other embodiments, the conductors can be any nonmagnetic electrically conductive material, such as silver or gold. The interior and exterior magnetic shielding 86 and 88 terminates at cap 32, leaving the twisted pair 84 to span the remaining distance from the end cap to the Helmholtz transformer 60 shown in FIG. 1. The interior magnetic shielding 86 is electrically connected to Faraday cage 16 through cap 32, while the exterior magnetic shielding is electrically connected to the magnetically shielded cage 40 shown in FIG. 1.

Referring to FIG. 1, the white noise generator 80 can generate nearly uniform noise across a frequency spectrum from zero to 100 kilohertz. In the illustrated embodiment, the filter 90 filters out noise above 50 kilohertz, but other frequency ranges may be used without departing from the spirit and scope of the invention.

White noise generator 80 is also electrically connected to the other input of dual trace oscilloscope 160 through patch cord 164.

Referring to FIGS. 1, 2 and 3, a sample of the substance 200 to be measured is placed on the sample tray 50 and the sample tray is placed within the faraday cage 10. In the first embodiment, the white noise generator 80 is used to inject white noise through the Helmholtz transformer 60. The noise signal creates an induced voltage in the gradiometer 110. The induced voltage in the gradiometer 110 is then detected and amplified by the SQUID 120, the output from the SQUID is further amplified by the flux locked loop 140 and sent to the SQUID controller 150, and then sent to the dual trace oscilloscope 160. The dual trace oscilloscope 160 is also used to display the signal generated by white noise generator 80.

The white noise signal is adjusted by altering the output of the white noise generator 80 and by rotating the Helmholtz transformer 60 around the sample 200, shown in FIG. 2. Rotation of the Helmholtz transformer 60 about the axis of the hinged connection of frames 66 and 68 alters its phasing with respect to the gradiometer 110. Depending upon the desired phase alteration, the hinged connection of frames 66 and 68 permits windings 62 and 64 to remain parallel to one another while rotating approximately 30 to 40 degrees around sample tray 50. The hinged connection also permits windings 62 and 64 to rotate as much as approximately 60 degrees out of parallel, in order to alter signal phasing of the field generated by Helmholtz transformer 60 with respect to gradiometer 110. The typical adjustment of phase will include this out-of-parallel orientation, although the other orientation may be preferred in certain circumstances, to accommodate an irregularly shaped sample 200, for example. Noise is applied and adjusted until the noise is 30 to 35 decibels above the molecular electromagnetic emissions sought to be detected. At this noise level, the noise takes on the characteristics of the molecular electromagnetic signal through the well-known phenomenon of stochastic resonance. The stochastic product sought is observed when the oscilloscope trace reflecting the signal detected by gradiometer 110 varies from the trace reflecting the signal directly from white noise generator 80. In alternative embodiments, the signal can be recorded and or processed by any commercially available equipment.

In an alternative embodiment, the method of detecting the molecular electromagnetic signals further comprises injecting noise 180° out of phase with the original noise signal applied at the Helmholtz transformer 60 through the noise suppression coil 124 of the SQUID 120. The stochastic product sought can then be observed when the oscilloscope trace reflecting the signal detected by gradiometer 110 becomes non-random.

Regardless of how the noise is injected and adjusted, the stochastic product can also be determined by observing when an increase in spectral peaks occurs. The spectral peaks can be observed as either a line plot on oscilloscope 160 or as numerical values, or by other well known measuring devices.

Embodiments of the present invention provide a method and apparatus for detecting extremely low-threshold molecular electromagnetic signals without external interference. They further provide for the output of those signals in a format readily usable by a wide variety of signal recording and processing equipment.

Figure 7:
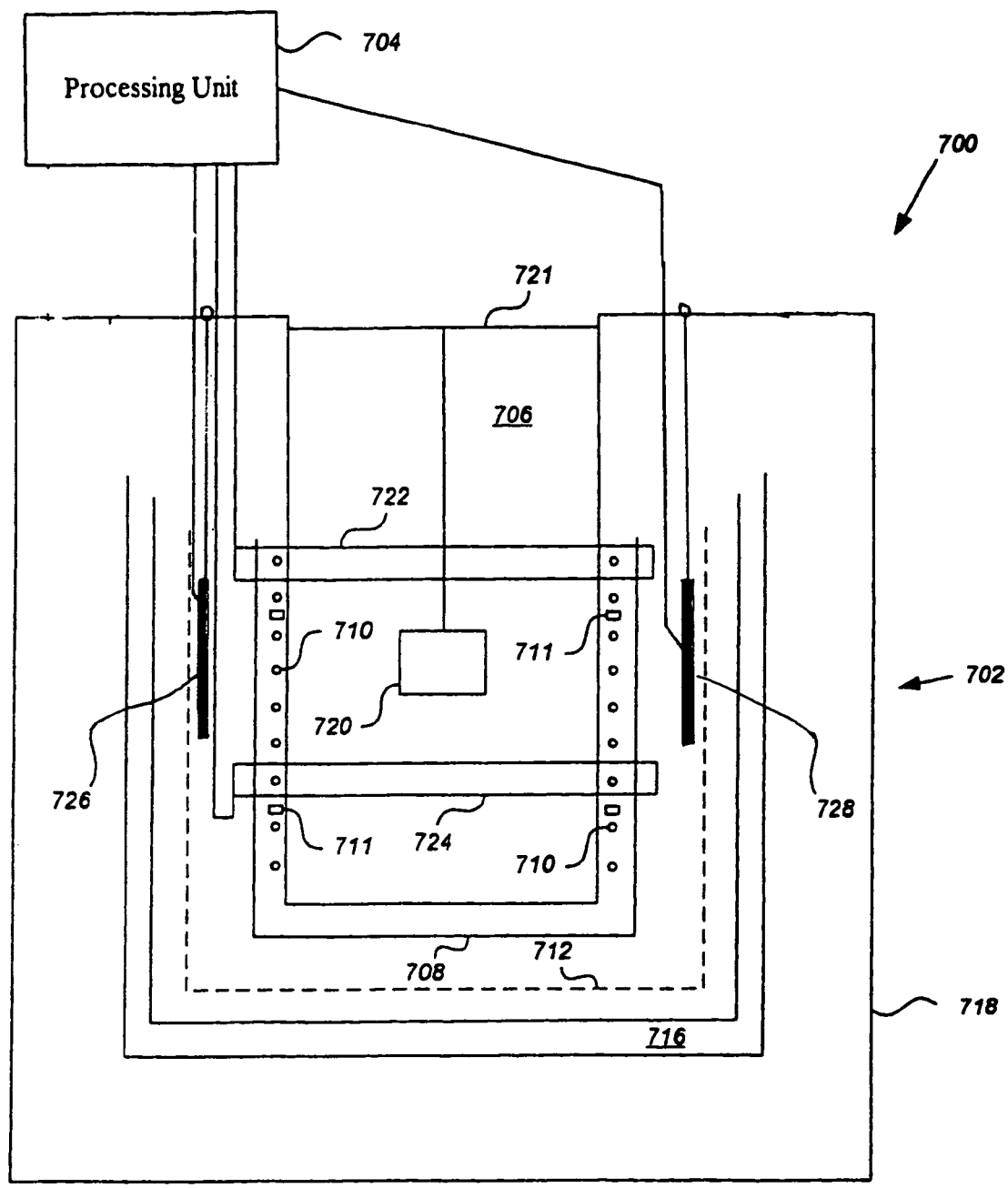
FIG. 7 is a diagram of an alternative electromagnetic emission detection system.

Referring now to FIG. 7, an alternative embodiment to the molecular electromagnetic emission detection and processing system of the above Figures is shown. A system 700 includes a detection unit 702 coupled to a processing unit 704. Although the processing unit 704 is shown external to the detection unit 702, at least a part of the processing unit can be located within the detection unit.

The detection unit 702, which is shown in a cross-sectional view in FIG. 7A, includes a plurality of components nested or concentric with each other. A sample chamber or faraday cage 706 is nested within a metal cage 708. Each of the sample chamber 706 and the metal cage 708 can be comprised of aluminum material. The sample chamber 706 can be maintained in a vacuum and may be temperature controlled to a preset temperature. The metal cage 708 is configured to function as a low pass filter.

Between the sample chamber 706 and the metal cage 708 and encircling the sample chamber 706 are a set of parallel heating coils or elements 710. One or more temperature sensor 711 is also located proximate to the heating elements 710 and the sample chamber 706. For example, four temperature sensors may be positioned at different locations around the exterior of the sample chamber 706. The heating elements 710 and the temperature sensor(s) 711 are configured to maintain a certain temperature inside the sample chamber 706.

A shield 712 encircles the metal cage 708. The shield 712 is configured to provide additional magnetic field shielding or isolation for the sample chamber 706. The shield 712 can be comprised of lead or other magnetic shielding materials. The shield 712 is optional when sufficient shielding is provided by the sample chamber 706 and/or the metal cage 708.

Surrounding the shield 712 is a cryogen layer 716 with G10 insulation. The cryogen may be liquid helium. The cryogen layer 716 (also referred to as a cryogenic Dewar) is at an operating temperature of 4 degrees Kelvin. Surrounding the cryogen layer 716 is an outer shield 718. The outer shield 718 is comprised of nickel alloy and is configured to be a magnetic shield. The total amount of magnetic shielding provided by the detection unit 702 is approximately −100 dB, −100 dB, and −120 dB along the three orthogonal planes of a Cartesian coordinate system.

The various elements described above are electrically isolated from each other by air gaps or dielectric barriers (not shown). It should also be understood that the elements are not shown to scale relative to each other for ease of description.

A sample holder 720 can be manually or mechanically positioned within the sample chamber 706. The sample holder 720 may be lowered, raised, or removed from the top of the sample chamber 706. The sample holder 720 is comprised of a material that will not introduce Eddy currents and exhibits little or no inherent molecular rotation. As an example, the sample holder 720 can be comprised of high quality glass or Pyrex.

The detection unit 702 is configured to handle solid, liquid, or gas samples. Various sample holders may be utilized in the detection unit 702. For example, depending on the size of the sample, a larger sample holder may be utilized. As another example, when the sample is reactive to air, the sample holder can be configured to encapsulate or form an airtight seal around the sample. In still another example, when the sample is in a gaseous state, the sample can be introduced inside the sample chamber 706 without the sample holder 720. For such samples, the sample chamber 706 is held at a vacuum. A vacuum seal 721 at the top of the sample chamber 706 aids in maintaining a vacuum and/or accommodating the sample holder 720.

A sense coil 722 and a sense coil 724, also referred to as detection coils, are provided above and below the sample holder 720, respectively. The coil windings of the sense coils 722, 724 are configured to operate in the direct current (DC) to approximately 50 kilohertz (kHz) range, with a center frequency of 25 kHz and a self-resonant frequency of 8.8 MHz. The sense coils 722, 724 are in the second derivative form and are configured to achieve approximately 100% coupling. In one embodiment, the coils 722, 724 are generally rectangular in shape and are held in place by G10 fasteners. The coils 722, 724 function as a second derivative gradiometer.

Helmholtz coils 726 and 728 may be vertically positioned within the shield 712, as explained herein. Each of the coils 726 and 728 may be raised or lowered independently of each other. The coils 726 and 728, also referred to as a white or Gaussian noise generation coils, are at room or ambient temperature. The noise generated by the coils 726, 728 is approximately 0.10 Gauss.

The degree of coupling between the emissions from the sample and the coils 722, 724 may be changed by repositioning the sample holder 720 relative to the coils 722, 724, or by repositioning one or both of the coils 726, 728 relative to the sample holder 720.

The processing unit 704 is electrically coupled to the coils 722, 724, 726, and 728. The processing unit 704 specifies the white or Gaussian noise to be injected by the coils 726, 728 to the sample. The processing unit 104 also receives the induced voltage at the coils 722, 724 from the sample's electromagnetic emissions mixed with the injected Gaussian noise.

Figure 8:
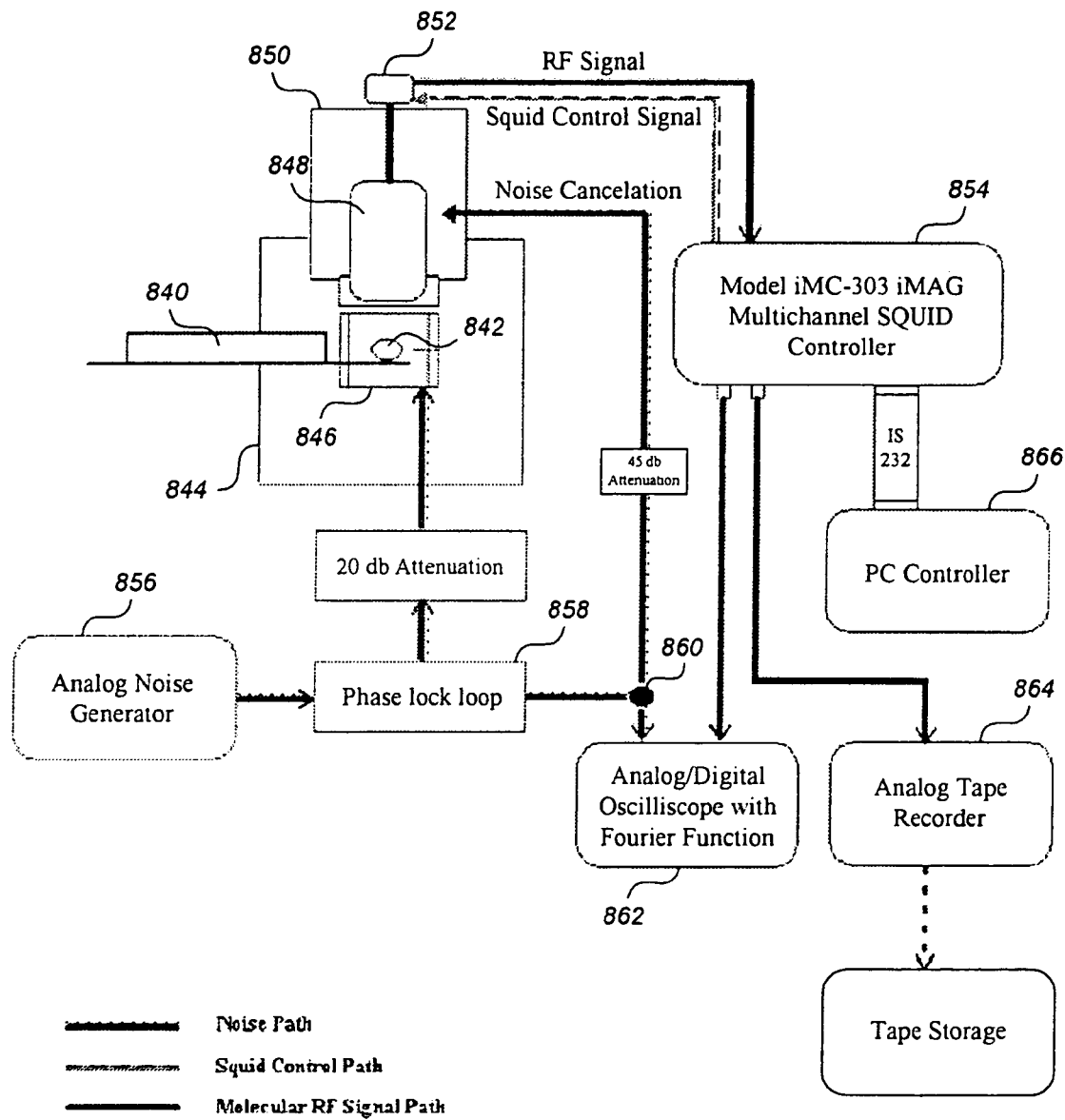
FIG. 8 diagram of the processing unit included in the detection system of the above Figures.

Referring to FIG. 8, a processing unit employing aspects of the invention includes a sample tray 840 that permits a sample 842 to be inserted into, and removed from, a Faraday cage 844 and Helmholtz coil 746. A SQUID/gradiometer detector assembly 848 is positioned within a cryogenic dewar 850. A flux-locked loop 852 is coupled between the SQUID/gradiometer detector assembly 848 and a SQUID controller 854. The SQUID controller 854 may be a model iMC-303 iMAG multichannel controller provided by Tristan.

An analog noise generator 856 provides a noise signal (as noted above) to a phase lock loop 858. The x-axis output of the phase lock loop is provided to the Helmholtz coil 846, and may be attenuated, such as by 20 dB. The y-axis output of the phase lock loop is split by a signal splitter 860. One portion of the y-axis output is input the noise cancellation coil at the SQUID, which has a separate input for the gradiometer. The other portion of the y-axis signal is input oscilloscope 862, such as an analog/digital oscilloscope having Fourier functions like the Tektronix TDS 3000b (e.g., model 30326). That is, the x-axis output of the phase lock loop drives the Helmholz coil, and the y-axis output, which is in inverted form, is split to input the SQUID and the oscilloscope. Thus, the phase lock loop functions as a signal inverter. The oscilloscope trace is used to monitor the analog noise signal, for example, for determining when a sufficient level of noise for producing non-stationary spectral components is achieved. An analog tape recorder or recording device 864, coupled to the controller 854, records signals output from the device, and is preferably a wideband (e.g. 50 kHz) recorder. A PC controller 866 may be an MS Windows based PC interfacing with the controller 854 via, for example, an RS 232 port.

Figure 9:
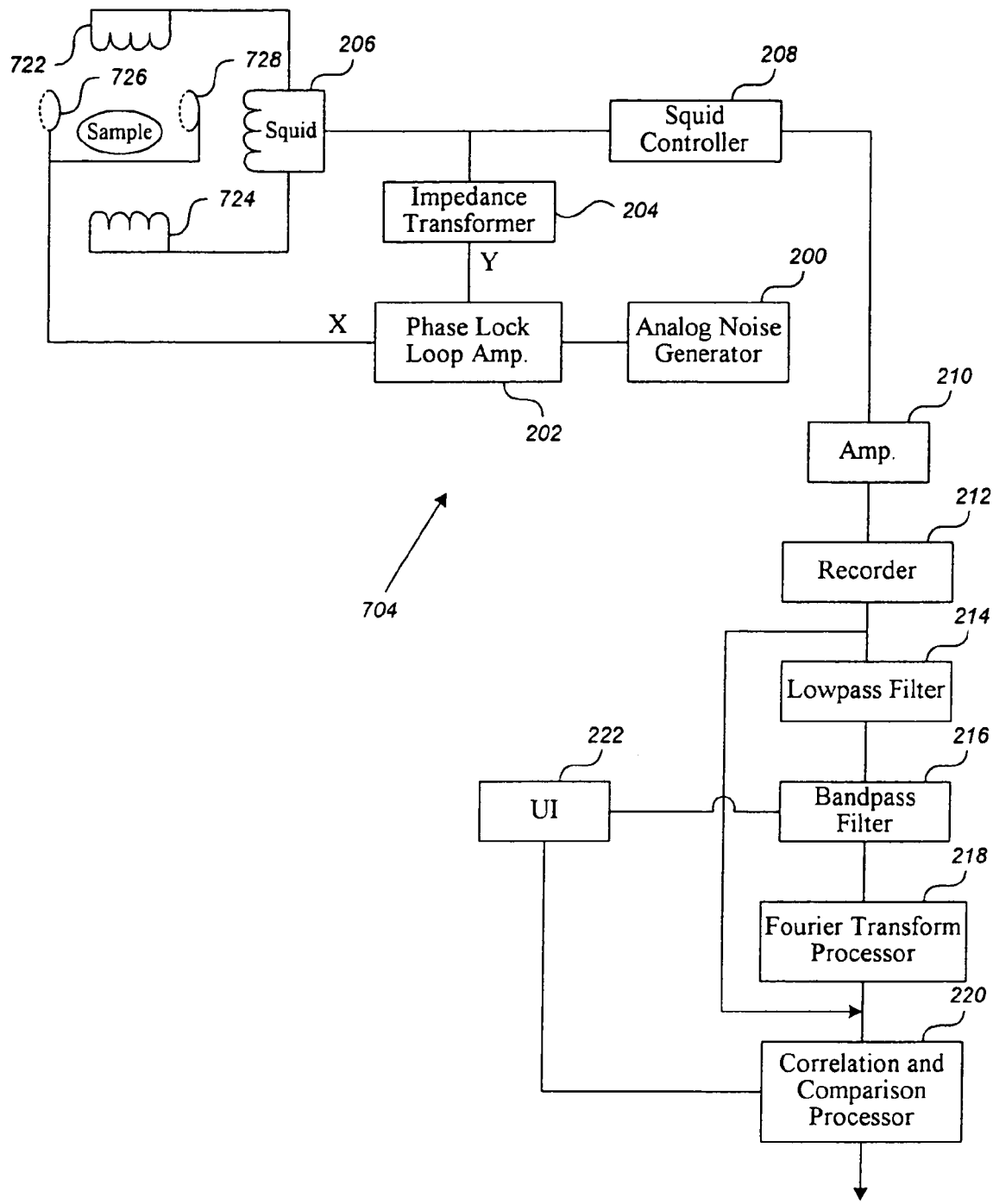
FIG. 9 is a diagram of an alternative processing unit to that of FIG. 8.

In FIG. 9, a block diagram of another embodiment of the processing unit is shown. A dual phase lock-in amplifier 202 is configured to provide a first signal (e.g., "x" or noise signal) to the coils 726, 728 and a second signal (e.g., "y" or noise cancellation signal) to a noise cancellation coil of a superconducting quantum interference device (SQUID) 206. The amplifier 202 is configured to lock without an external reference and may be a Perkins Elmer model 7265 DSP lock-in amplifier. This amplifier works in a "virtual mode," where it locks to an initial reference frequency, and then removes the reference frequency to allow it to run freely and lock to "noise."

An analog noise generator 200 is electrically coupled to the amplifier 202. The generator 200 is configured to generate or induce an analog white Gaussian noise at the coils 726, 728 via the amplifier 202. As an example, the generator 200 may be a model 1380 manufactured by General Radio.

An impedance transformer 204 is electrically coupled between the SQUID 206 and the amplifier 202. The impedance transformer 204 is configured to provide impedance matching between the SQUID 206 and amplifier 202.

The noise cancellation feature of the SQUID 206 can be turned on or off. When the noise cancellation feature is turned on, the SQUID 206 is capable of canceling or nullifying the injected noise component from the detected emissions. To provide the noise cancellation, the first signal to the coils 726, 728 is a noise signal at 20 dB above the molecular electromagnetic emissions sought to be detected. At this level, the injected noise takes on the characteristics of the molecular electromagnetic signal through stochastic resonance. The second signal to the SQUID 206 is a noise cancellation signal and is inverted from the first signal at an amplitude sufficient to null the noise at the SQUID output (e.g., 180 degrees out of phase with respect to the first signal).

The SQUID 206 is a low temperature direct element SQUID. As an example, the SQUID 206 may be a model LSQ/20 LTS dC SQUID manufactured by Tristan Technologies, Inc. Alternatively, a high temperature or alternating current SQUID can be used. The coils 722, 724 (e.g., gradiometer) and the SQUID 206 (collectively referred to as the SQUID/gradiometer detector assembly) combined has a magnetic field measuring sensitivity of approximately 5 microTesla/$\sqrt{Hz}$. The induced voltage in the coils 722, 724 is detected and amplified by the SQUID 206. The output of the SQUID 206 is a voltage approximately in the range of 0.2–0.8 microVolts.

The output of the SQUID 206 is the input to a SQUID controller 208. The SQUID controller 208 is configured to control the operational state of the SQUID 206 and further condition the detected signal. As an example, the SQUID controller 208 may be an iMC-303 iMAG multi-channel SQUID controller manufactured by Tristan Technologies, Inc.

The output of the SQUID controller 208 is inputted to an amplifier 210. The amplifier 210 is configured to provide a gain in the range of 0–100 dB. A gain of approximately 20 dB is provided when noise cancellation node is turned on at the SQUID 206. A gain of approximately 50 dB is provided when the SQUID 206 is providing no noise cancellation.

The amplified signal is inputted to a recorder or storage device 212. The recorder 212 is configured to convert the analog amplified signal to a digital signal and store the digital signal. In one embodiment, the recorder 212 stores 8600 data points per Hz and can handle 2.46 Mbits/sec. As an example, the recorder 212 may be a Sony digital audio tape (DAT) recorder. Using a DAT recorder, the raw signals or data sets can be sent to a third party for display or specific processing as desired.

A lowpass filter 214 filters the digitized data set from the recorder 212. The lowpass filter 214 is an analog filter and may be a Butterworth filter. The cutoff frequency is at approximately 50 kHz.

A bandpass filter 216 next filters the filtered data sets. The bandpass filter 216 is configured to be a digital filter with a bandwidth between DC to 50 kHz. The bandpass filter 216 can be adjusted for different bandwidths.

The output of the bandpass filter 216 is the input to a Fourier transformer processor 218. The Fourier transform processor 218 is configured to convert the data set, which is in the time domain, to a data set in the frequency domain. The Fourier transform processor 218 performs a Fast Fourier Transform (FFT) type of transform.

The Fourier transformed data sets are the input to a correlation and comparison processor 220. The output of the recorder 212 is also an input to the processor 220. The processor 220 is configured to correlate the data set with previously recorded data sets, determine thresholds, and perform noise cancellation (when no noise cancellation is provided by the SQUID 206). The output of the processor 220 is a final data set representative of the spectrum of the sample's molecular low frequency electromagnetic emissions.

A user interface (UI) 222, such as a graphical user interface (GUI), may also be connected to at least the filter 216 and the processor 220 to specify signal processing parameters. The filter 216, processor 218, and the processor 220 can be implemented as hardware, software, or firmware. For example, the filter 216 and the processor 218 may be implemented in one or more semiconductor chips. The processor 220 may be software implemented in a computing device.

This amplifier works in a "virtual mode," where it locks to an initial reference frequency, and then removes the reference frequency to allow it to run freely and lock to "noise." The analog noise generator (which is produced by General Radio, a truly analog noise generator) requires 20 dB and 45-dB attenuation for the Helmholz and noise cancellation coil, respectively.

The Helmholz coil may have a sweet spot of about one cubic inch with a balance of $\frac{1}{100}^{th}$ of a percent. In an alternative embodiments, the Helmholtz coil may move both vertically, rotationally (about the vertical access), and from a parallel to spread apart in a pie shape. In one embodiment, the SQUID, gradiometer, and driving transformer (controller) have values of 1.8, 1.5 and 0.3 micro-Henrys, respectively. The Helmholtz coil may have a sensitivity of 0.5 Gauss per amp at the sweet spot.

Approximately 10 to 15 microvolts may be needed for a stochastic response. By injecting noise, the system has raised the sensitivity of the SQUID device. The SQUID device had a sensitivity of about 5 femtotesla without the noise. This system has been able to improve the sensitivity by 25 to 35 dB by injecting noise and using this stochastic resonance response, which amounts to nearly a 1,500% increase.

After receiving and recording signals from the system, a computer, such as a mainframe computer, supercomputer or high-performance computer does both pre and post processing, such by employing the Autosignal software product by Systat Software of Richmond Calif., for the pre-processing, while Flexpro software product does the post-processing. Flexpro is a data (statistical) analysis software supplied by Dewetron, Inc. The following equations or options may be used in the Autosignal and Flexpro products.

Discrete Fourier Transform:

$$X_n = \sum_{k=0}^{N-1} {}_k e^{\frac{i2\pi k n}{N}}$$

Forward Transform $$X_k = 1 v \bigg/ \sum_{n=0}^{N-1} X_n e^{\frac{-i2\pi k n}{N}}$$

Reverse Transform

FFT Algorithm:

Best Exact N using Temperton's Prime Factor FFT (C. Temperton, "Implementation of a Self-Sorting In-Place Prime Factor FFT Algorithm, Journal of Computation Physics, v. 58, p. 283, 1985).

Data Tapering Windows:
[cs4 BHarris min] 0.35875-0.48829*cos(2*Pi*i/(n-1))+ 0.14128*cos(4*Pi*i/(n-1))-0.01168*(6*Pi*i/(n-1)), i=0.n-1
[Rectangular] No fixed shape tapering available (Oscilloscope)
Magnitude: sqrt(Re*Re+Im*Im) [Re=real component, Im=imaginary component]
Amplitude: 2.0*sqrt(Re*Re+Im*Im)/n
db, decibels: 10.0*log10(Re*Re+Im*Im)

Averaging Replicates:
Replicates are based on the X-values coinciding to within 1e-8 fractional precision.

Reference Subtraction:
Reference Signal Subtraction (baseline noise) is performed on Y axis (amplitude) at each point (channel) along the X (time) axis. Negative Y values are then zeroed.

Cross-Correlation:
The function calculates the cross correlation function using summation and integration. Since the signal is transient, the correlation function is calculated using direct multiplication and integration. All of the values required for the calculation which lie outside the source channels (data series) are taken to be 0. The points for which t<0 are also calculated.

Fourier Significance Levels:
Monte Carlo data is fitted to parametric models. Where data size N is the only factor, univariate TableCurve 2D parametric models are used. For a segmented FFT where segment size and overlap are additional influences, trivariate Chebyshev polynominals are implemented. These are options selected under Autosignal. One could have data sets that analyze individually, or could be analyzed in an overlapping fashion where data set one would be analyzed, then the second half of data set one and the first half of data set two, then data set two, then the second half.

Figure 10:
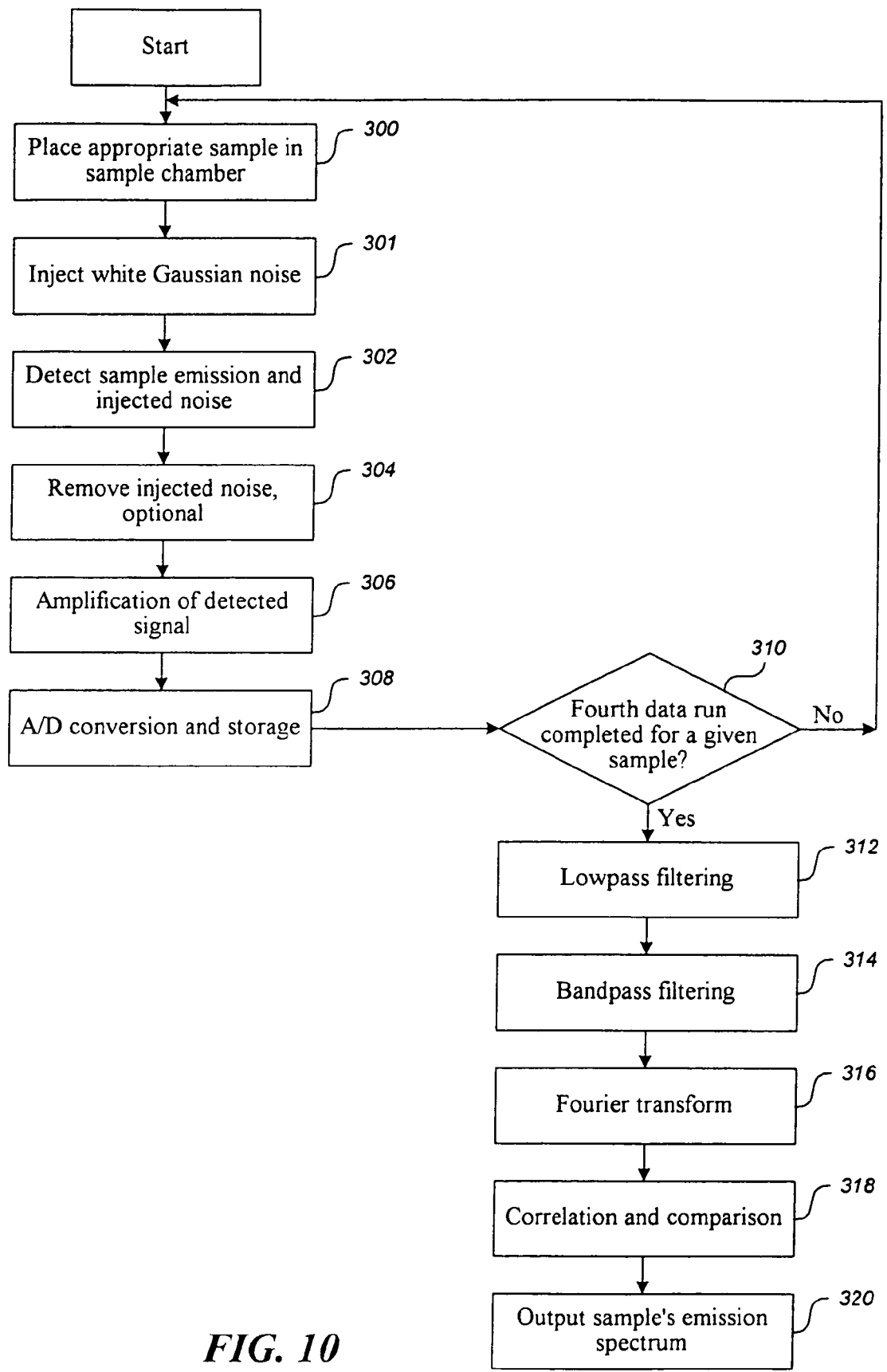
FIG. 10 is a flow diagram of the signal detection and processing performed by the present system.

A flow diagram of the signal detection and processing performed by the system 100 is shown in FIG. 10. When a sample is of interest, at least four signal detections or data runs are performed: a first data run at a time $t_1$ without the sample, a second data run at a time $t_2$ with the sample, a third data run at a time $t_3$ with the sample, and a fourth data run at a time $t_4$ without the sample. Performing and collecting data sets from more than one data run increases accuracy of the final (e.g., correlated) data set. In the four data runs, the parameters and conditions of the system 100 are held constant (e.g., temperature, amount of amplification, position of the coils, the noise signal, etc.).

At a block 300, the appropriate sample (or if it's a first or fourth data run, no sample), is placed in the system 100. A given sample, without injected noise, emits electromagnetic emissions in the DC-50 kHz range at an amplitude equal to or less than approximately 0.001 microTesla. To capture such low emissions, a white Gaussian noise is injected at a block 301.

At a block 302, the coils 722, 724 detect the induced voltage representative of the sample's emission and the injected noise. The induced voltage comprises a continuous stream of voltage values (amplitude and phase) as a function of time for the duration of a data run. A data run can be 2–20 minutes in length and hence, the data set corresponding to the data run comprises 2–20 minutes of voltage values as a function of time.

At a block 304, the injected noise is cancelled as the induced voltage is being detected. This block is omitted when the noise cancellation feature of the SQUID 206 is turned off.

At a block 306, the voltage values of the data set are amplified by 20–50 dB, depending on whether noise cancellation occurred at the block 304. And at a block 308, the amplified data set undergoes analog to digital (A/D) conversion and is stored in the recorder 212. A digitized data set can comprise millions of rows of data.

After the acquired data set is stored, at a block 310 a check is performed to see whether at least four data runs for the sample have occurred (e.g., have acquired at least four data sets). If four data sets for a given sample have been obtained, then lowpass filtering occurs at a block 312. Otherwise, the next data run is initiated (return to the block 300).

After lowpass filtering (block 312) and bandpass filtering (at a block 314) the digitized data sets, the data sets are converted to the frequency domain at a Fourier transform block 316.

Next, at a block 318, like data sets are correlated with each other at each data point. For example, the first data set corresponding to the first data run (e.g., a baseline or ambient noise data run) and the fourth data set corresponding to the fourth data run (e.g., another noise data run) are correlated to each other. IF the amplitude value of the first data set at a given frequency is the same as the amplitude value of the fourth data set at that given frequency, then the correlation value or number for that given frequency would be 1.0. Alternatively, the range of correlation values may be set at between 0–100. Such correlation or comparison also occurs for the second and third data runs (e.g., the sample data runs). Because the acquired data sets are stored, they can be accessed at a later time as the remaining data runs are completed.

When the SQUID 206 provides no noise cancellation, then predetermined threshold levels are applied to each correlated data set to eliminate statistically irrelevant correlation values. A variety of threshold values may be used, depending on the length of the data runs (the longer the data runs, greater the accuracy of the acquired data) and the likely similarity of the sample's actual emission spectrum to other types of samples. In addition to the threshold levels, the correlations are averaged. Use of thresholds and averaging correlation results in the injected noise component becoming very small in the resulting correlated data set.

If noise cancellation is provided at the SQUID 206, then the use of thresholds and averaging correlations are not necessary.

Once the two sample data sets have been refined to a correlated sample data set and the two noise data sets have been refined to a correlated noise data set, the correlated noise data set is subtracted from the correlated sample data set. The resulting data set is the final data set (e.g., a data set representative of the emission spectrum of the sample) (block 320).

Since there can be 8600 data points per Hz and the final data set can have data points for a frequency range of DC-50 kHz, the final data set can comprise several hundred million rows of data. Each row of data can include the frequency, amplitude, phase, and a correlation value.

Figure 11A:
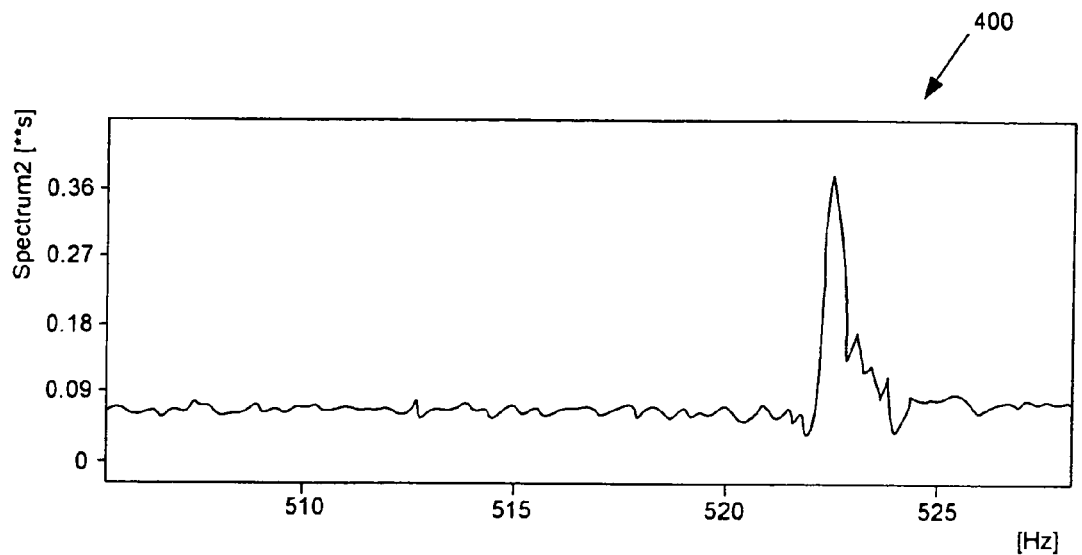
FIG. 11A is a spectral plot of the emissions of a first sample.
Figure 11B:
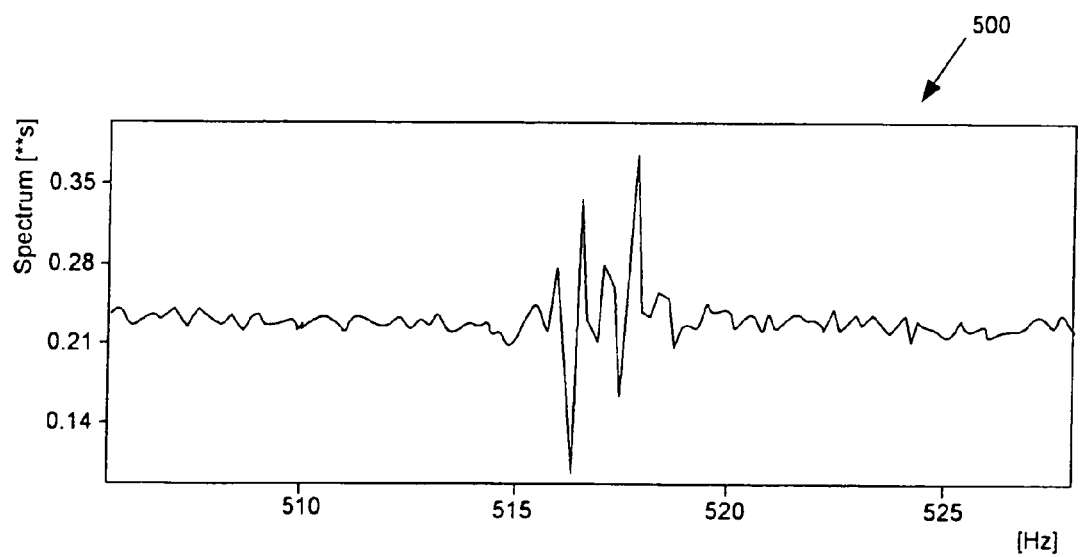
FIG. 11B is spectral plot of the emissions of a second sample.

In FIGS. 11A and 11B, there are shown examples of sample emission spectrums. A Fourier plot 400 shown in FIG. 11A corresponds to a spectrum of a sample of saturated sodium chloride solution. A Fourier plot 500 shown in FIG. 11B corresponds to a spectrum of a sample of an enzyme.

III. Methods and Applications

This section describes the use of the apparatus described above for interrogating a sample, and a variety of applications of the apparatus in characterizing a sample and in detecting sample components. Also disclosed, in accordance with the invention, is a low-frequency spectroscopic signature or data set by which a sample can be characterized, and a time-domain signal of a sample, used, for example, in generating the sample spectroscopic signature.

A. Method of Interrogating a Sample

An objective of the method of the invention is to generate spectroscopic information relating a sample being interrogated. As will be seen, the information may be in the form of a spectral plot, in a selected low-frequency spectral range, or a data set which identifies low-frequency spectral components characterizing the sample, or actual identification of a sample or sample components, based on the characteristic frequencies identified for the sample.

The sample may be any material having atomic or molecular components, e.g., ionic salt components or molecular compound in ionized or nonionized form, or protonated or non-protonated form, that has molecular rotation, and preferably a dipole moment such that molecular rotation in a magnetic field, e.g., the earth's magnetic field, is effective to produce a low-frequency electromagnetic emission. The sample is typically a liquid sample, but may be gaseous or solid or semi-solid as well, as long as at least one component of the sample has one or more rotational degrees of freedom. Typical samples are aqueous or organic solutions having one or more solute components, which may be the sample material of interest, dissolved in the solvent.

The sample is placed in a suitable vessel, preferably one such as pyrex glass that has little observable low-frequency spectral components, and the vessel is then positioned in the apparatus container as described in Section II. With the sample positioned in the apparatus container, the Gaussian noise generator is activated to inject Gaussian noise into the sample. The amplitude (mean amplitude) of Gaussian noise injected is preferably sufficient to produce non-stationary composite time-domain signal components. This may be done, for example, using an oscilloscope with a Fourier transform capability, and observing the frequency-domain signal in a suitable range, e.g., 200-800 Hz window. A suitable noise level is selected when detectable frequency components are first observed.

During noise injection, the recording device records a time-domain electromagnetic signal from the detector over a preset time interval. The recording interval may be relatively short, e.g., 30–40 seconds, or may be several minutes or more, depending on the final spectral resolution required. The signals recorded are stored in a suitable signal storage device, e.g., a tape or hard disc, for use in later signal processing operations now to be described.

In general, it is desirable to enhance sample signal components by cross-correlating the sample time-domain signal recorded with a second time-domain signal of the same sample or, less preferably, an identical sample or a sample having the same sample components of interest. The recording time for the second signal is preferably the same as for the first signal. The two signals are cross-correlated using a standard cross-correlation algorithm in the time domain. This results in a spreadsheet or spectrum identifying the signal spectral components that are common in both signals that hold up over time, and a correlation value for each component which measures the relationship between spectral components common to both signals.

The improvement in spectral resolution obtained by the signal cross-correlation is seen in the FIGS. 12A and 12B, and FIGS. 13A and 13B. The figures are Fast Fourier transforms of a first time-dependent signal in the frequency domain (FIGS. 12A and 13A) or a fast Fourier transform of the first and second cross-correlated frequency-domain spectra (the spreadsheet referred to above) (FIGS. 13B and 13B) to plot the spectral components in the frequency domain, and in the spectral range of 500–530 Hz.

Figure 12A:
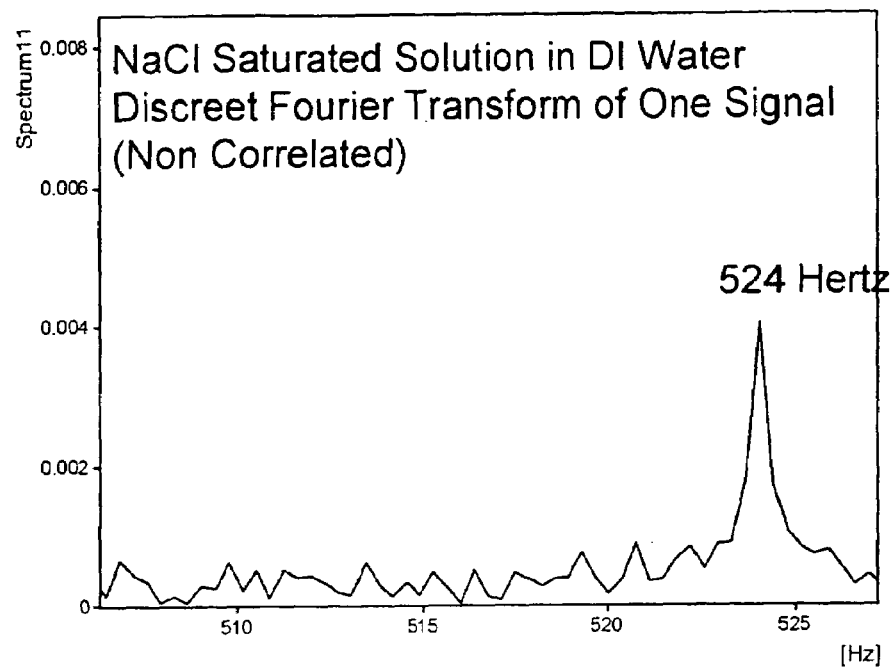
FIGS. 12A and 12B are spectral plots, in the spectral region between 500–530 Hz, for a sample of saturated NaCl, generated by Fourier transforming a non-correlated time-domain sample signal (12A), and Fourier transforming a cross-correlated sample spectrum (12B).
Figure 12B:
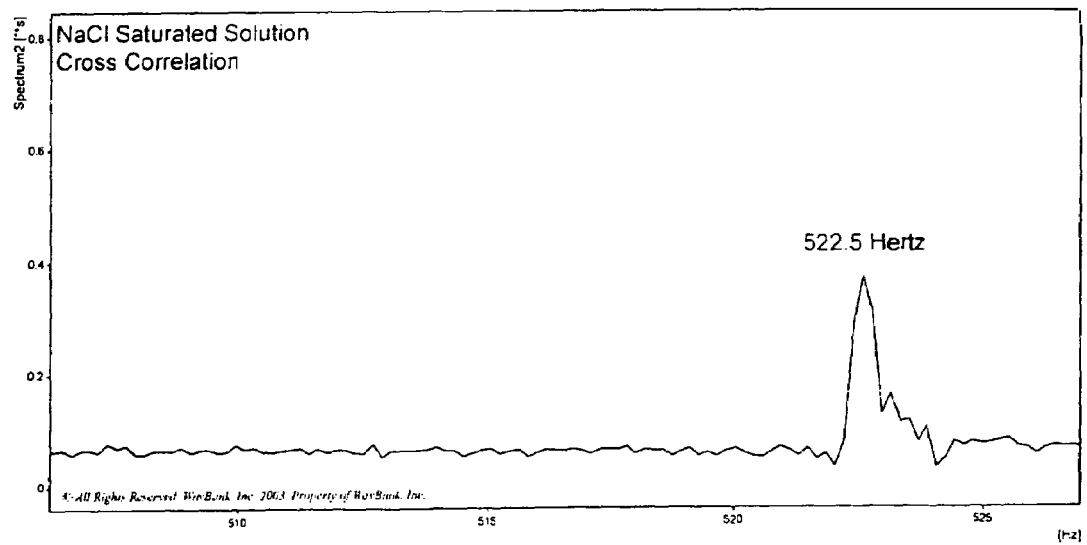
Figure 13A:
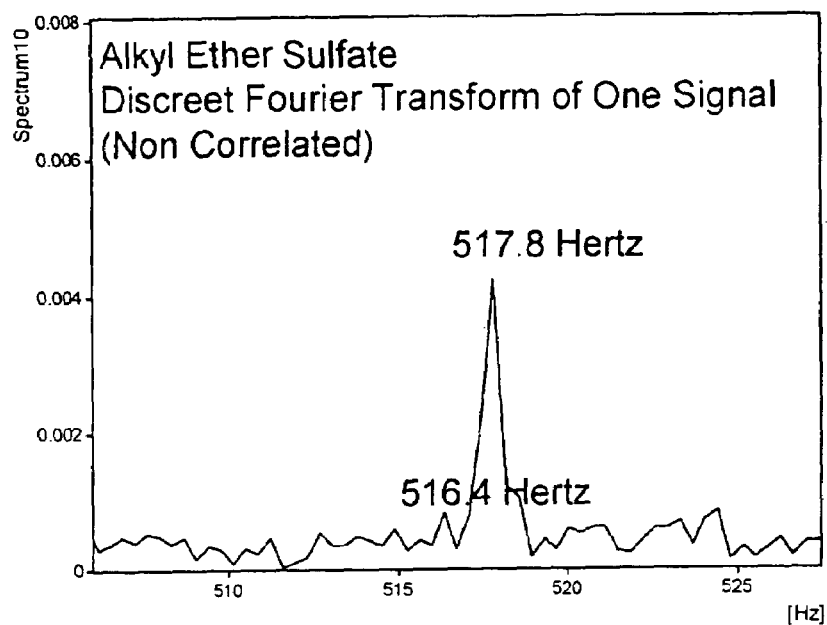
FIGS. 13A and 13B are spectral plots, in the spectral region between 500–530 Hz, for a sample of alkyl ether sulfate, generated by Fourier transforming a non-correlated time-domain sample signal (13A), and Fourier transforming a cross-correlated sample spectrum (13B).
Figure 13B:
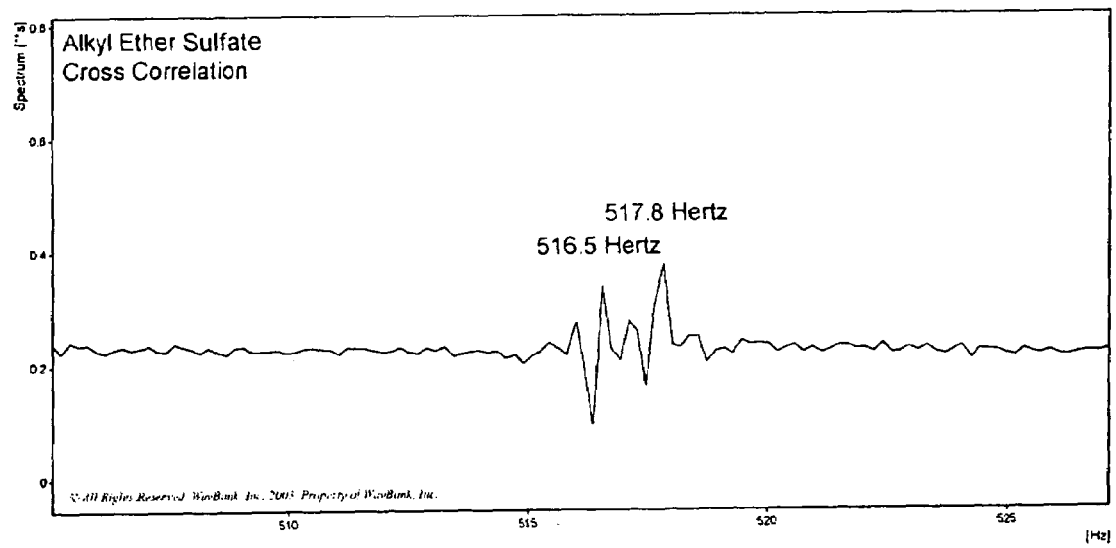
Figure 14A:
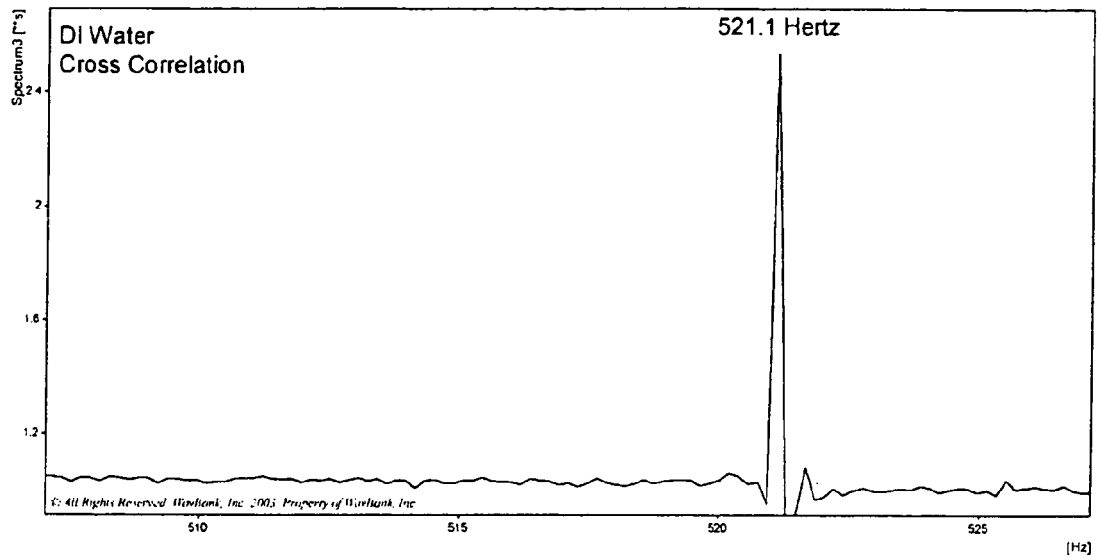
FIGS. 14A–14F are spectral plots, in the spectral region between 500–530 Hz, for samples of deionized water (14A), a saturated NaCl solution (14B), a solution of 1% NaCl in deionized water (14C); a saturated NaBr sample (14D), alkyl ether sulfate in deionized water (14E), and no sample (14F).
Figure 14B:
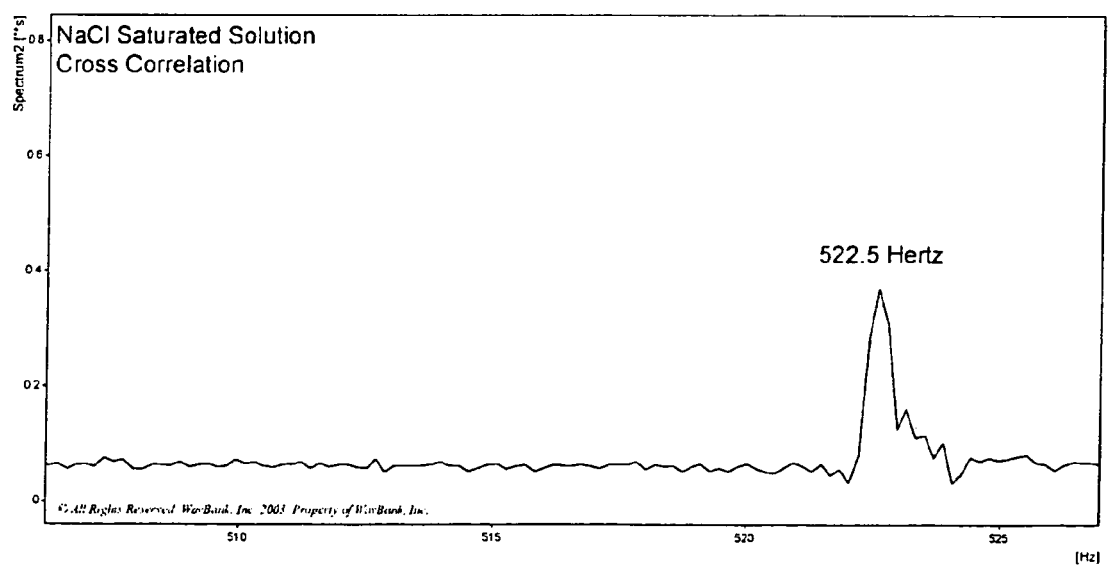
Figure 14C:
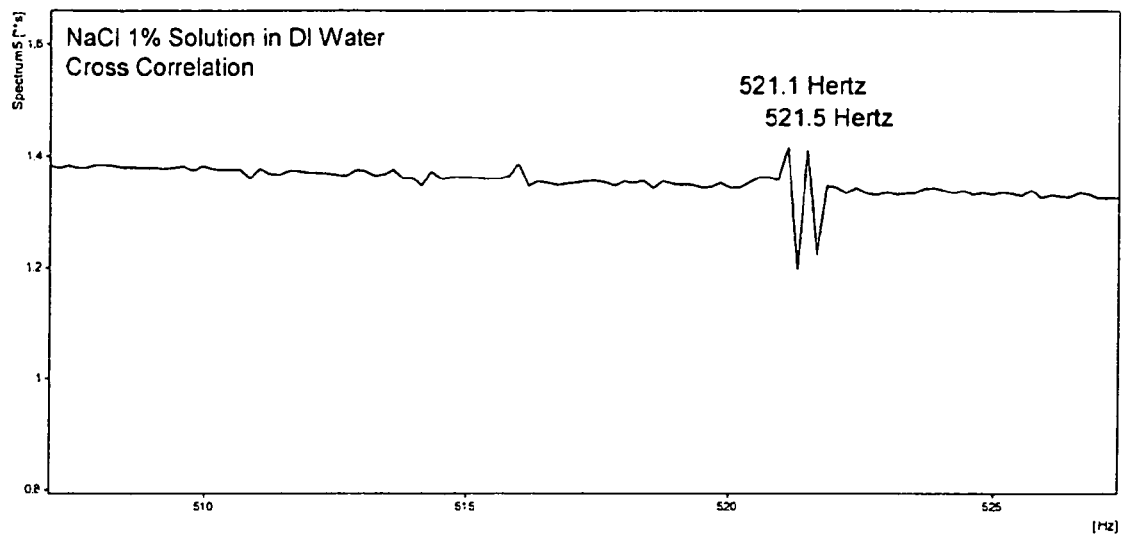
Figure 14D:
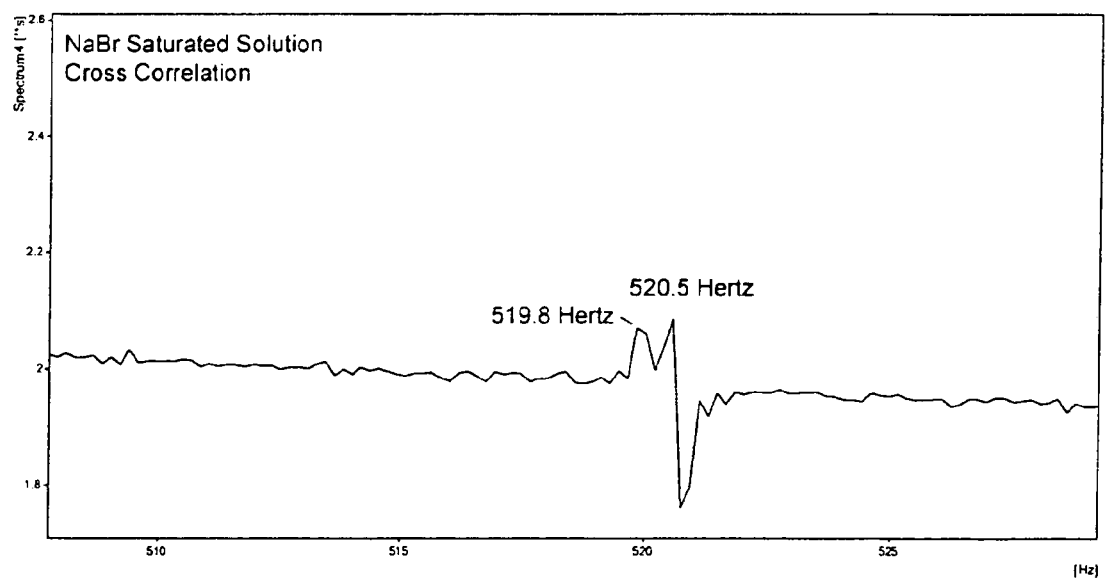
Figure 14E:
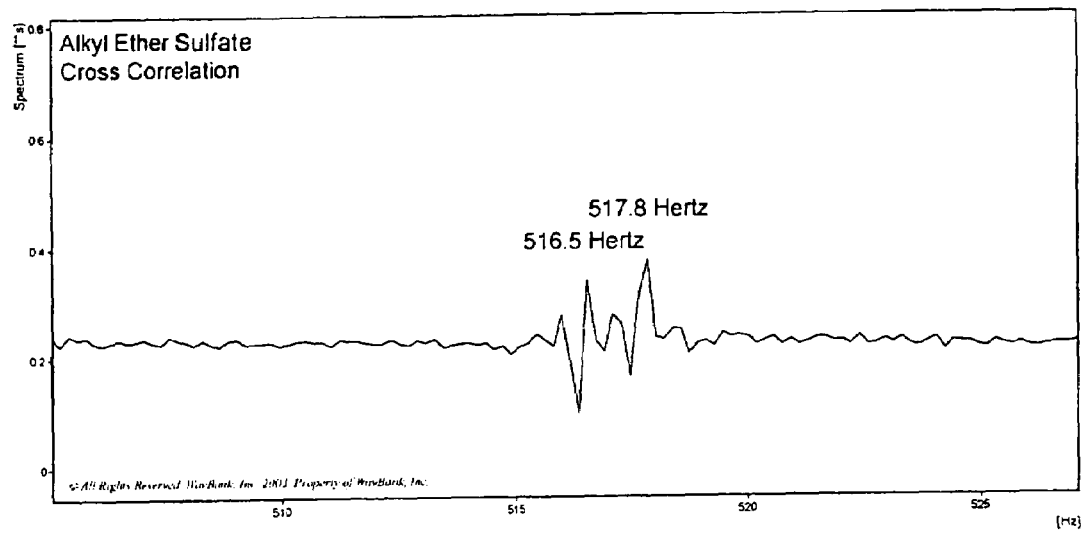
Figure 14F:
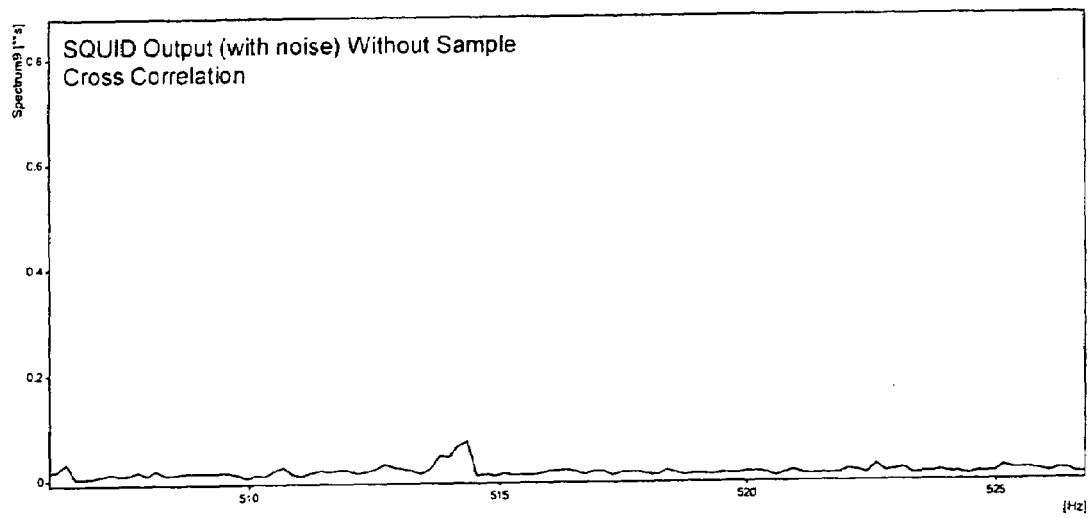
Figure 15A:
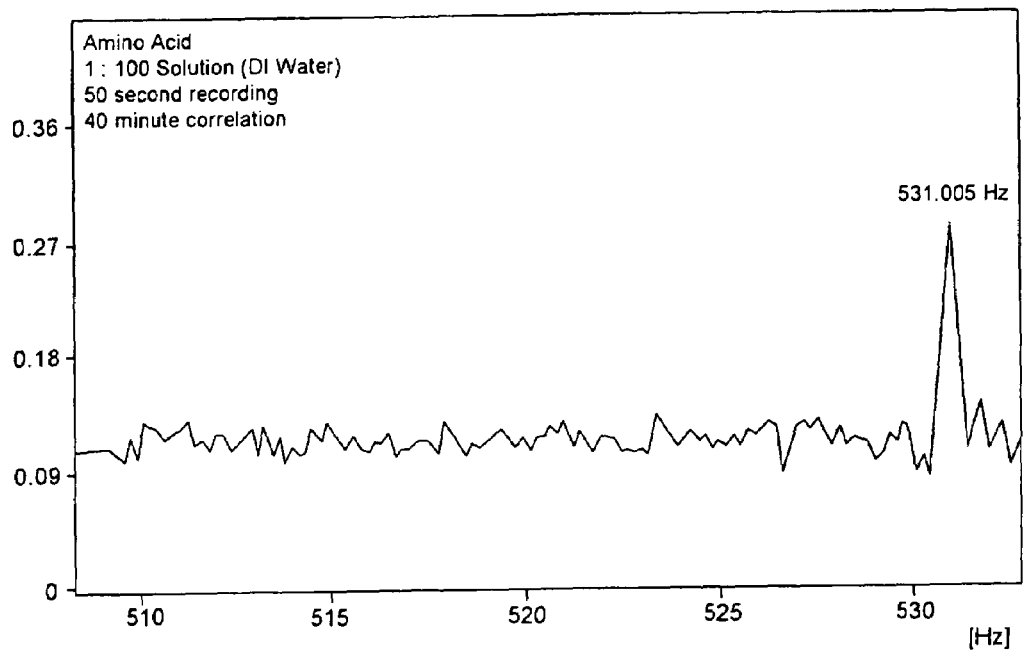
FIGS. 15A–15F are spectral plots, in the spectral region between 500 and 535 Hz, of a sample of an amino acid at a 1:100 wt/volume solution (15A) and at increasing w/v dilutions of 1:10,000 (15B), 1:1 million (15C), 1:100 million (15D), 1:10 billion (15E and 15F), where the spectra in FIGS. 15A–15E were generated with 50 second recordings and 40 minute correlations, and the spectrum of FIG. 15F was generated with a 4:25 minute recording with a 12 hour correlation.
Figure 15B:
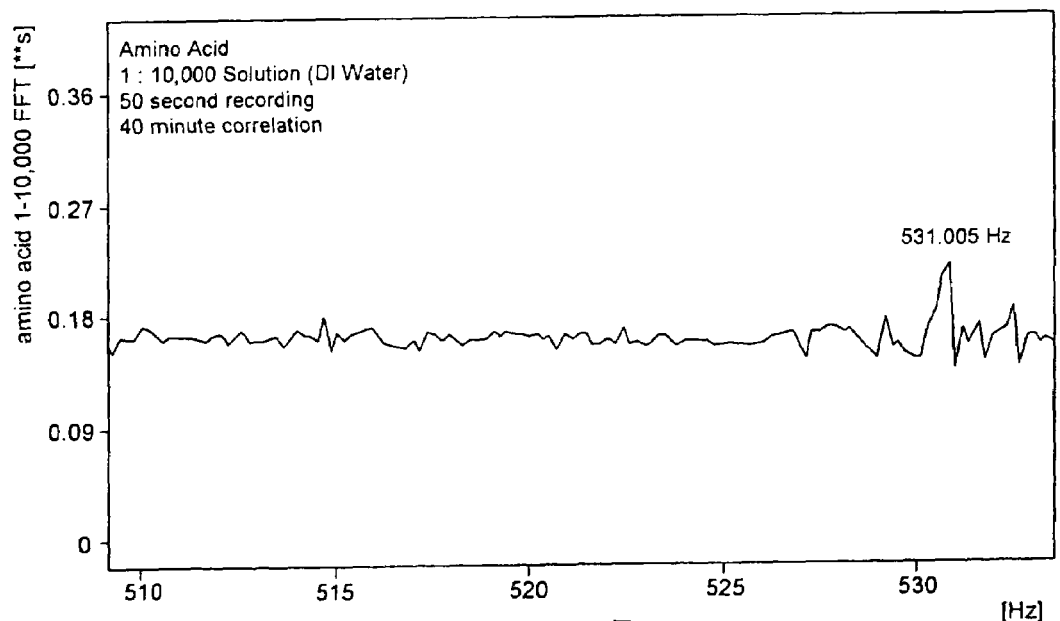
Figure 15C:
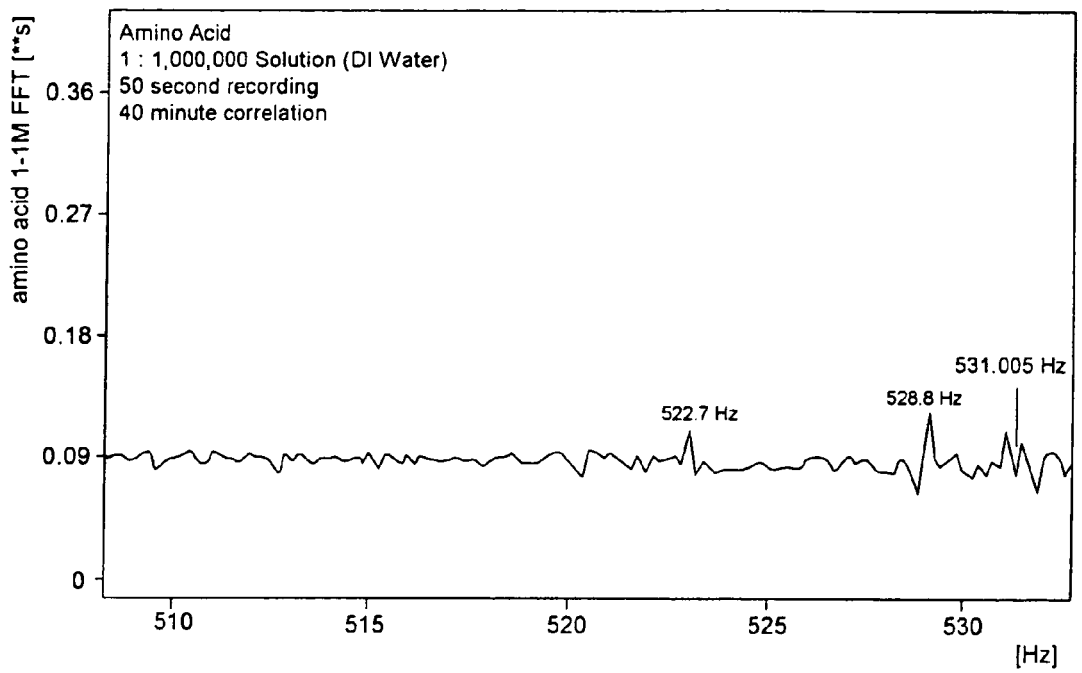
Figure 15D:
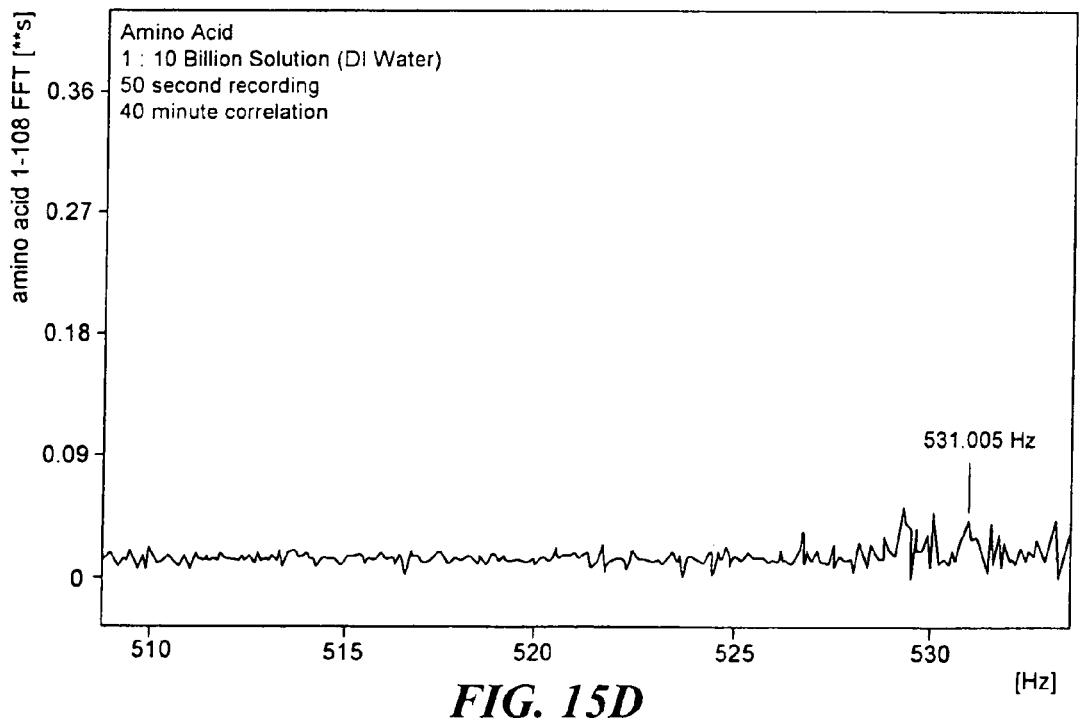
Figure 15E:
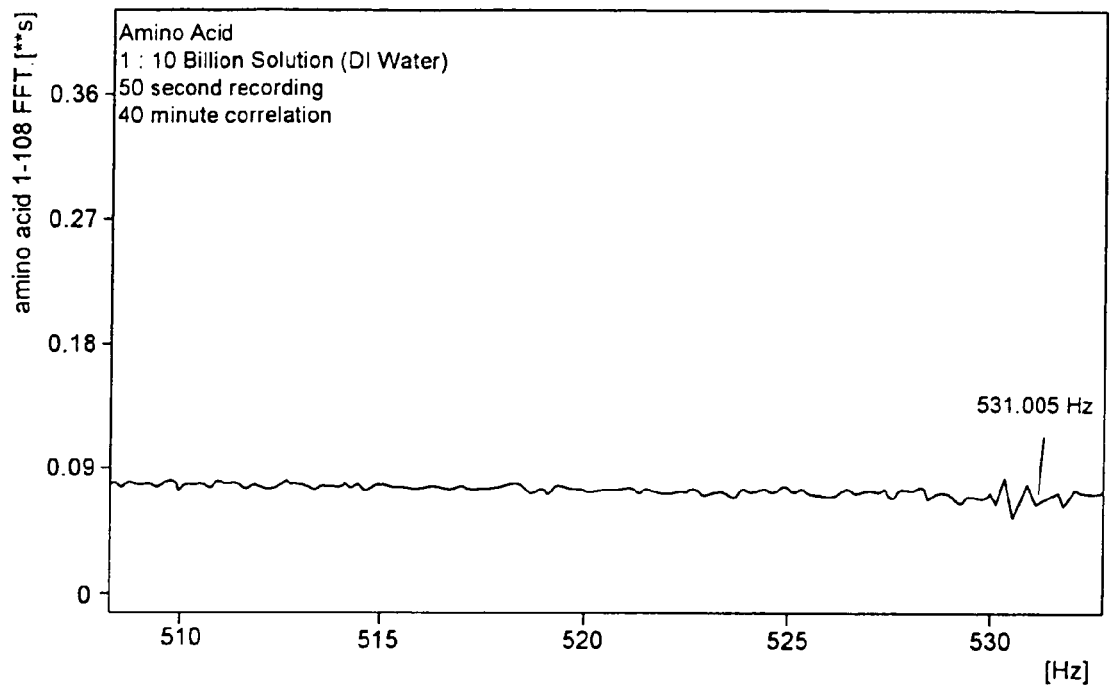
Figure 15F:
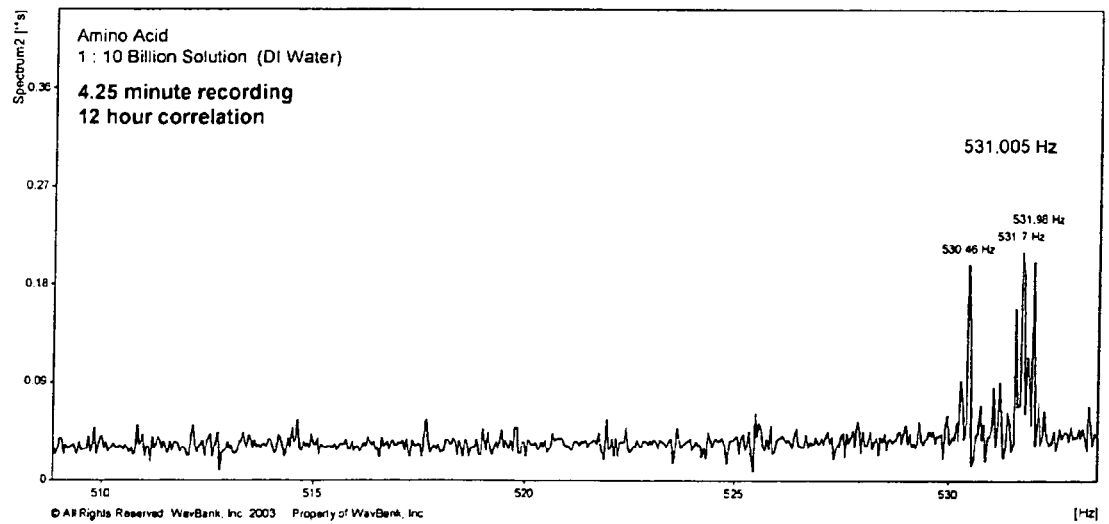

Comparing FIGS. 12A and 12B for a NaCl sample, it is seen that the cross-correlation signal processing significantly enhances signal-to-noise ratio, brings out much more detail in the sample-specific spectral component whose peak is at 522.5 Hz, and also produces a significantly refined peak position. Similar (and exemplary) results were observed for the alkyl ether sulfate sample, whose spectral features in the 500–530 Hz range are seen in FIGS. 13A and 13B for uncorrelated and correlated signals, respectively. As with the NaCl sample, the spectrum derived from the correlated signals gave much lower signal-to-noise ratio, much more detail and information as to sample-specific spectral components. The signal correlation can also be applied, conventionally, to produce a spreadsheet relating frequency and phase (rather than frequency and amplitude).

The correlated time-domain spectrum from above is plotted in the frequency domain by applying a fast Fourier transform to the spectrum, where the spectral correlations values are represented in the y axis as amplitudes. The plot is within the frequency range DC to 50 KHz, preferably in the region DC to 6.5 KHz. As will be seen below, the dominant spectral features of many samples are found in the 100–1,500 Hz range, particularly the 500–550 Hz range; and thus the spectrum generated may be confined accordingly, e.g., in the 500–530 Hz range. The FTT is carried out by a well known FTT algorithm. The correlated time-domain signal may also, or alternatively, be transformed to phase-domain or amplitude or magnitude domain signals, to extract signal information related to phase or amplitude components of the sample spectrum.

Once the frequency-domain spectrum is generated, either by the cross-correlating or FFT step, the spectrum is used to identify one or more low-frequency signal components that are characteristic of the sample being interrogated. This step may be performed by the user from direct viewing or by computer analysis of the spectra.

FIGS. 14A–14F show spectral features for the samples deionized water (FIG. 14A), saturated NaCl (FIG. 14B), 1% NaCl in deionized water (FIG. 14C), saturated NaBr (FIG. 14D), alkyl ether sulfate (FIG. 14E), and empty sample vessel (FIG. 14F), all in the spectral range of about 500–530. As seen, each sample has distinctive spectral components characterized by one or more peaks at well defined frequencies.

B. Characterizing a Sample

Accordance with another aspect of the invention, the method above is used to generate a data set of low-frequency spectral components of a given sample, also referred to herein as a low-frequency signature signal of the material.

The 500–530 spectral range shown for the several samples above was selected to illustrate having prominent spectral features in the various samples. In order to obtain a more complete data set of spectral frequency components of a sample, spectral components over a wider frequency range, e.g., 100–1,500 Hz, should be determined. In one aspect, the invention includes a data set of spectral components associated with a given sample material, e.g., a solvent, gas, or solute component of a solution. The data set includes a list of the low-frequency spectral components of the sample, e.g., in the 100–1,500 Hz range, whose cross-spectral correlations have a selected statistical measure above background spectral noise, or selected ones of these components that are unique to the sample.

A variety of signal-analysis methods may be employed in generating the low-frequency data set for a given sample. In one exemplary method, a cross-correlated sample signal spectrum is compared with a cross-correlated noise (no sample) signal. The algorithm next advances incremental, e.g., in 0.1 Hz intervals across the cross-correlated sample spectrum and the cross-correlated noise spectrum, looking at the correlation value at each frequency point, and subtracts the noise correlation from the sample correlation at that point, to yield a frequency plot of corrected correlation values. These values will be relative to a particular sample, and depend, for example, on the relative amplitude of any noise component.

In general, frequency components having a higher correlation value (relative to the other values in that sample) will tend to hold up (be observed) over many interrogations of the same sample. To identify those that do hold up, the frequency components observed for the sample over two or more sample sets, each obtained as above, are compared, and only those that are seen in two (or more, if available) sets are taken as valid components of the data set for that sample. In the tables below, data sets for several samples (as identified in the tables) are given along with the correlations determined from a single sample interrogation. Those values indicated in italics (typically having the smaller correlation values) were found not to hold up in multiple data sets from the same sample material.

Thus, for example, for the saturated NaCl sample in Table 1, spectral components at 522.58, 523.12, 523.47, and 523.85 Hz correlate from sample to sample, and would form a data set for the sample in the frequency range 500–530 Hz. Additional members of the data set may be included in an expanded frequency range.

Similarly, for the amino acid sample of Table 3, the data set would include components at 262.93, 257.81, 257.23, 536.68, 448.05, 531.37, 528.80, 593.44, 588.68, 583.74, 578.61, 769.59, and 744.14 in the frequency range of between about 250 and 1,400 Hz. The greater spectral composition of the amino acid sample, relative to NaCl, presumably reflects in part, the greater complexity of the sample molecule.

TABLE 1

| NaCl (Sat) Frequency/Correlation | | NaCl (1%) Frequency/Correlation | | NaBr (Sat) Frequency/Correlation | |
|---|---|---|---|---|---|
| ✓ | A | ✓ | A | ✓ | A |
| Reversing Noise → | | | | | |
| 522.58 | .3762 | 521.12 | 1.4161 | 520.57 | 2.0847 |
| 523.12 | .1732 | 521.48 | 1.4100 | 519.84 | 2.0704 |
| 523.47 | .1235 | 515.99 | 1.3865 | 509.37 | 2.0304 |
| 523.85 | .1021 | 520.75 | 1.3641 | 513.45 | 2.0155 |
| 507.38 | .0832 | 514.34 | 1.3735 | 516.35 | 1.9950 |
| 524.43 | .0768 | 525.86 | 1.3440 | 519.46 | 1.9950 |
| 512.71 | .0753 | 523.70 | 1.3400 | 518.33 | 1.9929 |
| — | — | 526.61 | 1.3364 | 522.78 | 1.9635 |

TABLE 2

| DI Water Frequency/Correlation | | Alkyl Ether Sulfate Frequency/Correlation | | Noise Frequency/Correlation | |
|---|---|---|---|---|---|
| ✓ | A | ✓ | A | ✓ | A |
| Reversing Noise → | | | | | |
| 521.12 | 1.5324 | 517.81 | .3376 | 514.34 | .0734 |
| 521.67 | 1.0818 | 516.50 | .3375 | 513.79 | .0432 |
| 520.20 | 1.0630 | 517.08 | .2776 | 506.28 | .0326 |
| 511.23 | 1.0502 | 515.46 | .2749 | 512.70 | .0277 |
| 515.44 | 1.0457 | 518.37 | .2508 | 522.58 | .0220 |
| 513.06 | 1.0451 | 519.47 | .2425 | 525.15 | .0177 |
| 525.51 | 1.0371 | 515.44 | .2400 | 516.36 | .0149 |
| 520.75 | 1.0301 | 519.84 | .2383 | 523.13 | .0140 |

TABLE 3

| Spectra Number | Frequency (Hz) | Correlation Factor |
|---|---|---|
| 1 | 262.93 | .139 |
| 2 | 340.39 | .134 |
| 3 | 257.81 | .126 |
| 4 | 357.23 | .114 |
| 5 | 417.48 | .110 |
| 6 | 536.68 | .101 |
| 7 | 448.05 | .096 |
| 8 | 531..37 | .096 |
| 9 | 528.80 | .077 |
| 10 | 593.44 | .071 |
| 11 | 588.68 | .065 |
| 12 | 583.74 | .058 |
| 13 | 1408.99 | .052 |
| 14 | 840.08 | .050 |
| 15 | 1393.99 | .048 |
| 16 | 578.61 | .045 |
| 17 | 1348.99 | .044 |
| 18 | 769.59 | .042 |

TABLE 3-continued

| Spectra Number | Frequency (Hz) | Correlation Factor |
|---|---|---|
| 19 | 1042.96 | .042 |
| 20 | 1238.52 | .042 |
| 21 | 1472.16 | .042 |
| 22 | 1062.92 | .041 |
| 23 | 1281.73 | .041 |
| 24 | 744.14 | .039 |

The data above demonstrates that both simple and more complex molecular samples can be characterized in terms of unique low-frequency spectral components. The data set associated with a given sample material may also include (as shown in the tables) the associated correlations values of the spectral components. The data set may be used for example, in identifying components in an unknown sample and/or for estimating the relative concentrations of a material in a sample. The use of the method for identifying low-concentration components in a sample is discussed in the next section.

C. Identifying Components in a Sample

It is often desirable to detect sample components, e.g., trace contaminants, present in a multi-component sample material, such as a liquid sample with unknown contaminants, or other samples capable of holding or supporting a contaminant that it is desired to detect.

An analytical method for detecting a component of a sample, in accordance with another aspect of the invention, includes first identifying the low-frequency sample spectral components of a sample (i) in a selected frequency range between DC and 50 KHz (ii) whose cross-spectral correlations have a selected statistical measure above background spectral noise, as described above.

The sample spectral components are then compared with characteristic low-frequency spectral components of known compounds suspected of being present in the sample. In a typical example, the sample components are compared against the data set of each of the components suspected of being in the sample and which one desires to detect. A components, e.g., compound is identified as being present in the sample if one or more of its characteristic low-frequency spectral components correspond to one or more low-frequency spectral components of a known sample.

As shown in the set of FIGS. 11A–11F, detection of a compound (an amino acid) can occur at very low levels, e.g., in the parts per billion range or lower. In particular, even at a dilution of 1:10 billion w/v, a characteristic spectral component at about 531 Hz is observed. The figures demonstrate that signal amplitude, corresponding spectral component correlation, does decline with increasing compound dilution. However, the loss in signal amplitude at low concentration can be compensated for by extending the recording time, in this example, from 50 seconds for the first group of figures to 4.25 minutes for the most dilute sample (FIG. 11F).

Where, as in the above example, the spectral component amplitude declines with decreasing concentration, the amount of compound can be estimated on the basis of signal amplitude, assuming that the data set for the compound also includes concentration dependent amplitude information.

It has also been observed in some cases that the frequency of the characteristic spectral components may shift by as much as 3 Hz in a systematic fashion with changes in concentration. For such compounds, the amount of material present in a sample can be estimated by changes in amplitude and/or frequency shift in one or more of the spectral components. It will be appreciated for materials showing a concentration dependent frequency shift that a data set for that compound could include concentration-dependent frequencies as well as concentration-dependent amplitudes for particular components.

D. Time-domain Signals

In still another aspect, the invention includes a time-domain signal associated with a material of interest. The time-domain signal, and its method of production, have been discussed above. Briefly, the signal is produced by placing the sample of interest in a container having both magnetic and electromagnetic shielding, injecting Gaussian noise into the sample; and recording an electromagnetic time-domain signal composed of sample source radiation superimposed on the injected Gaussian noise.

The signal may be used to characterize a sample, much as a spectral component data set is used to characterize a material. Alternatively, the signal may be used for generating a low frequency signal signature of spectral components associated with a material of interest. The signal signature can be generated, also as described above, by (i) cross correlating the time-domain signal recorded with a second time domain signal separately recorded from the same or similar sample, to produce a frequency domain spectrum in a frequency range within DC to 50 Khz.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

What is claimed is:

1. Apparatus for interrogating a sample that exhibits molecular rotation, comprising:
   a container adapted for receiving the sample, the container having both magnetic and electromagnetic shielding;
   a source of noise for injection into the sample, with the sample in the container;
   a detector for detecting an electromagnetic time-domain signal composed of sample source radiation superimposed on the injected Gaussian noise;
   a storage device for storing the time-domain signal and a second time-domain signal separately detected from the same or a similar sample; and
   an electronic computer which is adapted to receive the stored signal from the storage device, and to process the signal by:
   (i) cross correlating the time-domain signal detected with the second time-domain signal, to produce a frequency-domain spectrum in a frequency range within DC to 50 KHz, and
   (ii) generating an output that includes information relating to spectral components in the spectrum that are characteristic of the sample.

2. The apparatus of claim 1, wherein the container is an attenuation tube having a sample-holding region, a magnetic shielding cage surrounding the region, and a Faraday cage contained within the magnetic shielding cage and also surrounding the region.

3. The apparatus of claim 1, wherein the sample container includes a temperature controller for maintaining the sample in the container at a selected temperature.

4. The apparatus of claim 1, wherein the source of noise includes a Gaussian noise generator and a Helmholz coil which is contained within the magnetic cage and the Faraday cage, and which receives a noise output signal from the noise generator.

5. The apparatus of claim 4, wherein the noise generator is designed to inject stationary white Gaussian noise into the sample, at an amplitude sufficient to produce non-stationary composite signal components.

6. The apparatus of claim 5, wherein the noise generator is designed to inject Gaussian noise into the sample at a frequency between DC and 2 KHz.

7. The apparatus of claim 1, wherein the detector is a first-derivative superconducting gradiometer which outputs a current signal, and a SQUID operatively connected to the gradiometer to convert the current signal to an amplified voltage signal.

8. The apparatus of claim 7, wherein the container is an attenuation tube having a sample-holding region, a magnetic shielding cage surrounding the region, and a Faraday cage contained within the magnetic shielding cage and also surrounding the region, the source of noise includes a Gaussian noise generator and a Helmholz coil which is contained within the magnetic cage and the Faraday cage, and which receives a noise output signal from the noise generator, and which further includes, for use in removing stationary noise components in the time-dependent signal, a signal inverter operatively connected to the noise source and to the SQUID, for receiving Gaussian noise from the noise source and outputting into the SQUID, Gaussian noise in inverted form with respect to the Gaussian noise injected into the sample.

9. The apparatus of claim 1, wherein the computer is operable to generate a frequency-domain spectrum in a range between DC to 6.5 Kz.

10. The apparatus of claim 9, wherein the computer is operable, to produce a frequency-domain signal in a range between 100 and 1,200 Hz.

11. The apparatus of claim 1, wherein the computer is operable, in generating an output, of identifying frequencies of low-frequency signal components in the spectrum whose cross-spectral correlations have a selected statistical measure above background spectral noise.

12. The apparatus of claim 11, for use in characterizing a known sample material in terms of its low-frequency signal components, wherein the computer is operable, in generating an output, of identifying material-specific low-frequency spectral components in the spectrum whose cross-spectral correlations have a selected statistical measure above background spectral noise.

13. The apparatus of claim 12, for use in identifying one or more components in a sample, wherein the computer is operable, in generating an output, to (a) identify frequencies of sample signal components (i) in a selected frequency range between DC and 50 KHz (ii) whose cross-spectral correlations have a selected statistical measure above background spectral noise, (b) compare such sample signal components with characteristic low-frequency signal components of known compounds suspected of being present in the sample, and (c) identify a compound as being present in the sample if its characteristic low-frequency signal frequencies correspond to those one or more of the sample-signal frequencies.

14. A method for interrogating a sample that exhibits molecular rotation, comprising:
placing the sample in a container having both magnetic and electromagnetic shielding;
injecting noise into the sample;
recording an electromagnetic time-domain signal composed of sample source radiation superimposed on the injected noise;
comparing the time-domain signal recorded with a second time domain signal separately recorded from the same or similar sample, to produce a frequency domain spectrum in a frequency range within DC to 50 Khz; and
identifying in the frequency-domain spectrum, one or more low-frequency signal components that are characteristic of the sample being interrogated.

15. The method of claim 14, wherein the injecting includes generating Gaussian noise from a noise generator and injecting the noise into the sample by means of a Helmholz coil which is located within the container.

16. The method of claim 15, wherein the injecting includes injecting stationary white Gaussian noise into the sample, at an amplitude sufficient to produce non-stationary composite signal components.

17. The method of claim 16, wherein the noise injected into the sample has a frequency between DC and 2 KHz.

18. The method of claim 14, wherein the detecting includes capturing the composite signal with a first-derivative superconducting gradiometer and converting the gradiometer signal to an amplified voltage signal by a SQUID.

19. The method of 18, wherein the container is an attenuation tube having a sample-holding region, a magnetic shielding cage surrounding the region, and a Faraday cage contained within the magnetic shielding cage and also surrounding the region, the noise is injected from a Gaussian noise generator and a Helmholz coil which is contained within the magnetic cage and the Faraday cage, and which receives a noise output signal from the noise generator, and which further includes, for use in removing stationary noise components in the time-dependent signal, a signal inverter operatively connected to the the noise source and to the SQUID, for receiving Gaussian noise from the noise source and outputting into the SQUID, Gaussian noise in inverted form with respect to the Gaussian noise injected into the sample.

20. The method of claim 14, which further includes transforming a cross-correlated frequency-domain spectrum to produce a frequency-domain spectral plot in a range between DC to 6.5 Kz.

21. The method of claim 20, which further includes transforming a cross-correlated frequency-domain spectrum to produce a frequency-domain spectral plot in a range between 100 and 1,200 Hz.

22. The method of claim 14, for use in characterizing a known sample material according to frequencies of its low-frequency signal components, which further includes identifying frequencies of sample-specific spectral components (i) in a selected frequency range between DC and 50 KHz (ii) whose cross-spectral correlations have a selected statistical measure above background spectral noise.

23. The method of claim 14, for use in identifying one or more components in a sample, which further includes (a) identifying the frequencies of sample spectral components (i) in a selected frequency range between DC and 50 KHz (ii) whose cross-spectral correlations have a selected statistical measure above background spectral noise, (b) comparing such sample spectral components with characteristic low-frequency spectral components of known compounds suspected of being present in the sample, and (c) identifying a compound as being present in the sample if one or more of its characteristic low-frequency spectral components correspond to one or more low-frequency spectral components of a known sample.

24. The method of claim 23, wherein the sample component is present in a liquid sample at a concentration between 1 part per million and 1 part per 10 billion.

25. The method of claim 24, wherein one or more of the low-frequency signal components of a compound exhibits a concentration-dependent frequency shift of less than 2 Hz, and the identifying includes approximating the concentration of a sample component by its frequency shift.

26. The method of claim 24, wherein one or more of the low-frequency signal components of a compound exhibits a concentration-dependent cross-spectral correlation, the identifying includes approximating the concentration of a sample component by its cross-spectral correlation.

27. A time-domain signal associated with a material of interest, produced by:

placing the sample of the material in a container having both magnetic and electromagnetic shielding, injecting Gaussian noise into the sample; and recording an electromagnetic time-domain signal composed of sample source radiation superimposed on the injected Gaussian noise, correlating the time-domain signal recorded with a second time domain signal separately recorded from the same or similar sample, to produce a correlated time-domain signal, and transforming the time-domain signal to a frequency domain spectrum in a frequency range within DC to 50 Khz, and identifying in the frequency-domain spectrum, one or more low-frequency signal components that are characteristic of the sample being interrogated.

* * * * *

UNITED STATES PATENT AND TRADEMARK OFFICE
CERTIFICATE OF CORRECTION

PATENT NO. : 7,081,747 B2
APPLICATION NO. : 10/923545
DATED : July 25, 2006
INVENTOR(S) : John T. Butters et al.

It is certified that error appears in the above-identified patent and that said Letters Patent is hereby corrected as shown below:

<u>Column 16</u>
Line 18, "30-40 seonds" should be --30-60 seconds--.

Signed and Sealed this

Twenty-first Day of November, 2006

JON W. DUDAS
*Director of the United States Patent and Trademark Office*